United States Patent
Bossi et al.

(10) Patent No.: US 9,250,213 B1
(45) Date of Patent: *Feb. 2, 2016

(54) ULTRASOUND INSPECTION SYSTEM FOR INSPECTING A TEST OBJECT WITH NON-PLANAR FEATURES

(75) Inventors: Richard H. Bossi, Renton, WA (US); Gary E. Georgeson, Tacoma, WA (US); Clarence L. Gordon, III, Renton, WA (US); Jeffrey R. Kollgaard, Seattle, WA (US); William P. Motzer, Seattle, WA (US); Alan Frank Stewart, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 288 days.

This patent is subject to a terminal disclaimer.

(21) Appl. No.: 13/596,977

(22) Filed: Aug. 28, 2012

Related U.S. Application Data

(63) Continuation-in-part of application No. 13/526,853, filed on Jun. 19, 2012.

(51) Int. Cl.
*G01N 29/24* (2006.01)
*G01N 29/265* (2006.01)
*G01N 21/17* (2006.01)

(52) U.S. Cl.
CPC ........ *G01N 29/2418* (2013.01); *G01N 21/1702* (2013.01); *G01N 29/265* (2013.01); *G01N 2291/2694* (2013.01)

(58) Field of Classification Search
CPC ....... G01N 29/06; G01N 29/26; G01N 29/04; G01N 29/28; G01N 29/2418; G01N 2291/044; G01N 2291/0231; G01N 29/265; G01N 29/343; G01N 2291/106; G01N 29/24; G01N 2291/2694; G01N 21/17; G01N 21/1702; G06F 19/321
USPC ........... 73/643, 655, 596, 627, 620, 621, 634, 73/584, 622, 865.8, 657; 378/57; 356/502
See application file for complete search history.

(56) References Cited

U.S. PATENT DOCUMENTS

| | | | | |
|---|---|---|---|---|
| 3,327,584 A | * | 6/1967 | Kissinger | G01B 11/026 250/227.28 |
| 4,010,636 A | * | 3/1977 | Clark et al. | G01M 3/24 376/249 |

(Continued)

FOREIGN PATENT DOCUMENTS

| | | |
|---|---|---|
| EP | 1744156 A2 | 1/2007 |
| EP | 2345881 A1 | 7/2011 |

(Continued)

OTHER PUBLICATIONS

Georgeson et al., "Ultrasound Inspection System of Limited Access Composite Structures," U.S. Appl. No. 13/526,698, filed Jun 19, 2012, (74 Pages).

(Continued)

*Primary Examiner* — Laura Martin
*Assistant Examiner* — Rose M Miller
(74) *Attorney, Agent, or Firm* — Yee & Associates, P.C.

(57) ABSTRACT

A method and apparatus for inspecting a test object. The apparatus comprises an inspection vehicle, a sensor structure, a first array of optical fibers, and a second array of optical fibers. The inspection vehicle is configured to move on a surface of the test object. The sensor structure is associated with the inspection vehicle. The first array of optical fibers is associated with the sensor structure. The first array of optical fibers is configured to transmit a pattern of light towards the surface of the test object and the pattern of light is configured to cause sound waves in the test object when the pattern of light encounters the test object. The second array of optical fibers is associated with the sensor structure. The second array of optical fibers is configured to detect a response to the sound waves.

12 Claims, 27 Drawing Sheets

(56) References Cited

U.S. PATENT DOCUMENTS

| | | | |
|---|---|---|---|
| 4,160,386 A * | 7/1979 | Jackson et al. | G01N 29/223 367/117 |
| 4,295,738 A | 10/1981 | Meltz et al. | |
| 4,379,409 A * | 4/1983 | Primbsch et al. | G10K 15/046 385/100 |
| 4,567,769 A | 2/1986 | Barkhoudarian | |
| 5,473,953 A | 12/1995 | Appel | |
| 5,760,904 A | 6/1998 | Lorraine et al. | |
| 6,003,377 A | 12/1999 | Waag et al. | |
| 6,087,652 A * | 7/2000 | O'Meara et al. | G01D 5/26 250/208.1 |
| 6,144,685 A | 11/2000 | Iwasa et al. | |
| 6,901,157 B2 | 5/2005 | Ogawa | |
| 7,042,563 B2 | 5/2006 | Wilsher et al. | |
| 7,369,250 B2 | 5/2008 | Dubois et al. | |
| 7,576,848 B2 | 8/2009 | Dubois et al. | |
| 7,643,893 B2 | 1/2010 | Troy et al. | |
| 7,743,660 B2 | 6/2010 | Marsh et al. | |
| 7,784,348 B2 * | 8/2010 | Dubois et al. | 73/621 |
| 7,791,739 B2 | 9/2010 | Dubois et al. | |
| 7,800,762 B2 | 9/2010 | Deaton, Jr. et al. | |
| 7,859,655 B2 | 12/2010 | Troy et al. | |
| 7,865,316 B2 | 1/2011 | Turner et al. | |
| 8,044,991 B2 | 10/2011 | Lea et al. | |
| 8,109,160 B2 | 2/2012 | Bossi et al. | |
| 8,196,817 B2 | 6/2012 | Lourenco et al. | |
| 8,198,617 B2 | 6/2012 | Georgeson et al. | |
| 8,224,485 B2 | 7/2012 | Unsworth | |
| 8,249,832 B2 | 8/2012 | Motzer et al. | |
| 8,279,412 B2 | 10/2012 | Motzer et al. | |
| 8,312,773 B2 * | 11/2012 | Fomitchov | 73/643 |
| 8,347,746 B2 | 1/2013 | Hafenrichter et al. | |
| 2003/0043964 A1 | 3/2003 | Sorenson | |
| 2003/0147493 A1 | 8/2003 | Bueno et al. | |
| 2004/0003662 A1 | 1/2004 | Kenderian et al. | |
| 2005/0274188 A1 | 12/2005 | Cabanis et al. | |
| 2006/0055396 A1 | 3/2006 | Georgeson et al. | |
| 2006/0055399 A1 | 3/2006 | Georgeson et al. | |
| 2006/0132804 A1 * | 6/2006 | Dubois et al. | G01N 21/1702 356/614 |
| 2008/0307886 A1 | 12/2008 | Marsh et al. | |
| 2009/0086014 A1 | 4/2009 | Lea et al. | |
| 2010/0139405 A1 | 6/2010 | Melikechi et al. | |
| 2010/0154549 A1 | 6/2010 | Fomitchov | |
| 2010/0291599 A1 | 11/2010 | Tague, Jr. et al. | |
| 2011/0137615 A1 | 6/2011 | Motzer et al. | |
| 2011/0149266 A1 | 6/2011 | Motzer et al. | |
| 2011/0178727 A1 | 7/2011 | Hafenrichter et al. | |
| 2012/0221625 A1 | 8/2012 | Troy et al. | |
| 2012/0304774 A1 * | 12/2012 | Ishioka | 73/643 |
| 2012/0320372 A1 | 12/2012 | Troy et al. | |
| 2013/0018525 A1 | 1/2013 | Jang et al. | |
| 2013/0047731 A1 * | 2/2013 | Ume et al. | G01N 29/2418 73/643 |

FOREIGN PATENT DOCUMENTS

| | | |
|---|---|---|
| GB | 2057697 A | 4/1981 |
| GB | 2491978 A | 12/2012 |

OTHER PUBLICATIONS

Bossi et al., "Ultrasound Inspection System for Inspecting a Test Object with Non-Planar Features," U.S. Appl. No. 13/526,853, filed Jun. 19, 2012, (62 Pages).

Bossi et al., "Laser Ultrasound Array System," U.S. Appl. No. 13/527,021, filed Jun. 19, 2012, (62 Pages).

Fomitchov et al., "Laser Ultrasonic Array System for Real-Time Cure Monitoring of Polymer-Matrix Composites," Journal of Composite Materials, vol. 36, No. 15, Aug. 2002, pp. 1889-1901.

Wang et al., "Beam shaping technology for laser diode arrays," Proceedings of SPIE, vol. 4770, Jul. 2002, pp. 131-135.

Office Action, dated Jun. 3, 2013, regarding U.S. Appl. No. 13/160,238, 17 pages.

Final Office Action, dated Oct. 29, 2013, regarding U.S. Appl. No. 13/160,238.

Notice of Allowance, dated Dec. 16, 2013, regarding U.S. Appl. No. 13/160,238, 7 pages.

UK Combined Search and Examination Report, dated Oct. 10, 2012, regarding Application No. GB1210632.4, 6 pages.

Final Office Action, dated Oct. 6, 2014, regarding U.S. Appl. No. 13/526,698, 33 pages.

Final Office Action, dated Oct. 22, 2014, regarding U.S. Appl. No. 13/526,853, 28 pages.

Final Office Action, dated Oct. 28, 2014, regarding U.S. Appl. No. 13/527,021, 33 pages.

Office Action, dated May 8, 2014, regarding U.S. Appl. No. 13/526,698, 31 pages.

Office Action, dated Jun. 26, 2014, regarding U.S. Appl. No. 13/527,021, 28 pages.

Office Action, dated Jun. 6, 2014, regarding U.S. Appl. No. 13/526,853, 33 pages.

Intellectual Property Office of Singapore Search Report and Written Opinion, dated Jul. 3, 2014, regarding Application No. 201304652-9, 12 pages.

Office Action, dated Apr. 15, 2015, regarding U.S. Appl. No. 13/526,853, 16 pages.

Office Action, dated Apr. 15, 2015, regarding U.S. Appl. No. 13/527,021, 17 pages.

Notice of Allowance, dated Jun. 5, 2015, regarding U.S. Appl. No. 13/527,021, 11 pages.

Office Action, dated Apr. 14, 2015, regarding U.S. Appl. No. 13/526,698, 17 pages.

Notice of Allowance, dated Jul. 7, 2015, regarding U.S. Appl. No. 13/526,698, 9 pages.

Office Action, dated Jan. 30, 2015, regarding U.S. Appl. No. 13/526,698, 32 pages.

Office Action, dated Jan. 5, 2015, regarding U.S. Appl. No. 13/527,021, 25 pages.

Notice of Allowance, dated Sep. 4, 2015, regarding U.S. Appl. No. 14/149,887, 21 pages.

* cited by examiner

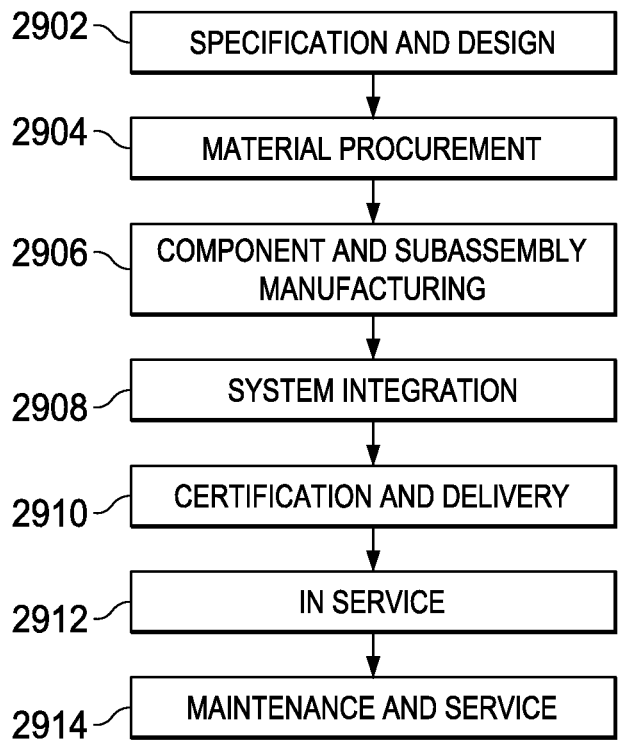
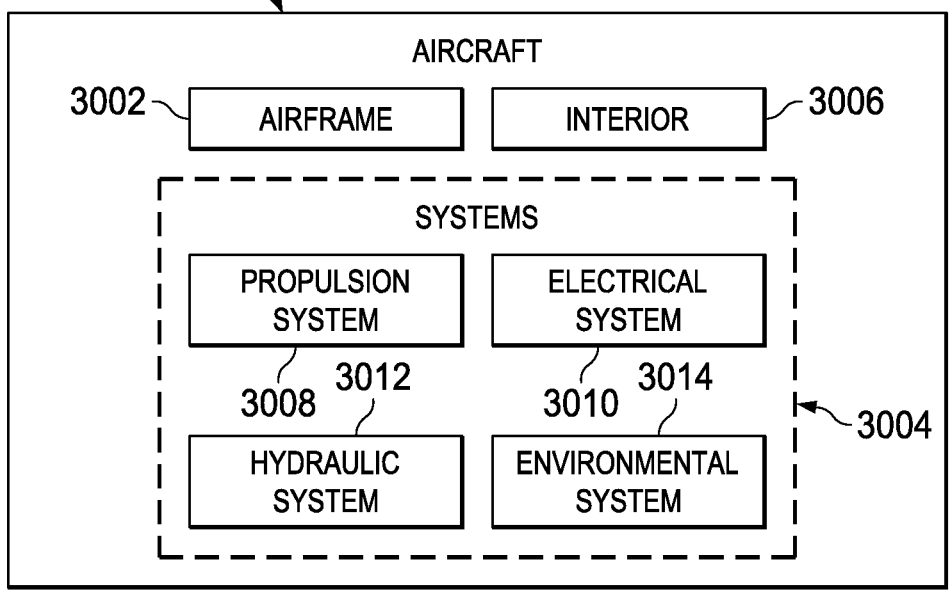

ULTRASOUND INSPECTION SYSTEM FOR INSPECTING A TEST OBJECT WITH NON-PLANAR FEATURES

CROSS-REFERENCE TO RELATED APPLICATIONS

This application is a continuation-in-part of patent application U.S. Ser. No. 13/526,853, filed Jun. 19, 2012, entitled "Ultrasound Inspection System for Inspecting a Test Object with Non-planar Features," which is incorporated herein by reference.

This application is also related to the following patent applications, entitled: "Laser Ultrasound Array System," U.S. Ser. No. 13/527,021, filed Jun. 19, 2012; "Ultrasound Inspection System of Limited Access Composite Structures," U.S. Ser. No. 13/526,698, United States Patent Application Publication Number 2013/0333472, filed Jun. 19, 2012; and "Autonomous Non-Destructive Evaluation System for Aircraft Structures," U.S. Ser. No. 13/160,238, filed Jun. 14, 2011, United States Patent Application Publication Number 2012/0320372; which are incorporated herein by reference.

BACKGROUND INFORMATION

1. Field

The present disclosure relates generally to inspecting objects and, in particular, to performing non-destructive inspection of objects. Still more particularly, the present disclosure relates to a method and apparatus for inspecting objects using ultrasound.

2. Background

In manufacturing aircraft, vehicles, and other structures, inspection of parts used to form these structures is often performed to determine whether the parts will have desired parameters for a desired performance of the part. Non-destructive testing is commonly performed on these parts. Non-destructive testing is used to evaluate properties of a part without altering the ability of the part to be employed in service. Non-destructive testing may include ultrasound testing, eddy current testing, x-ray testing, visual inspections, and other types of testing.

Ultrasound testing is often used to perform inspections on aircraft parts that include or are comprised of composite materials. Ultrasound testing involves transmitting sound waves through a test object. A response to these sound waves is detected. The response is analyzed to determine whether inconsistencies are present in the test object.

Ultrasound testing is commonly performed using a transducer. The transducer is configured to send sound waves into a test object and detect a response to the sound waves. The transducer is typically coupled to a surface of the test object. This coupling involves physical contact between the transducer and the test object.

In many cases, a coupling medium is also employed. For example, water, oil, a water-based gel, or some other liquid may be used. This coupling medium is used to reduce the acoustic impedance between the transducer and the test object.

In some cases, coupling the transducer to the surface of the test object may be more difficult to perform than desired. Difficulty in coupling a transducer to the surface of the test object may occur when the test object has a non-planar surface. In other words, the surface of the test object may have non-planar features. The non-planar feature may be a radius, an edge, a curve, an angle, or other types of non-planar features. When non-planar features are present on the surface of a test object, more difficulty may occur than desired when attempting to ensure that sound enters the test object in a direction that is substantially perpendicular to the surface of the test object. For layered materials such as carbon fiber laminates, perpendicular sound entry is particularly desirable during the inspection process.

Further, the use of a coupling medium may be undesirable with some test objects. For example, the use of a coupling medium may take more time and effort than desired or may be detrimental to the test object.

Therefore, it would be desirable to have a method and apparatus that takes into account at least some of the issues discussed above, as well as other possible issues.

SUMMARY

In one illustrative embodiment, an apparatus comprises an inspection vehicle, a sensor structure, a first array of optical fibers, and a second array of optical fibers. The inspection vehicle is configured to move on a surface of a test object. The sensor structure is associated with the inspection vehicle. The first array of optical fibers is associated with the sensor structure. The first array of optical fibers is configured to transmit a pattern of light towards the surface of the test object and the pattern of light is configured to cause sound waves in the test object when the pattern of light encounters the test object. The second array of optical fibers is associated with the sensor structure. The second array of optical fibers is configured to detect a response to the sound waves.

In another illustrative embodiment, a non-destructive inspection system for an aircraft comprises an inspection vehicle, a sensor structure, a first array of optical fibers, a second array of optical fibers, a positioning system, a support system, and a controller. The inspection vehicle is configured to move on a surface of the aircraft. The sensor structure is associated with the inspection vehicle. The first array of optical fibers is associated with the sensor structure. The first array of optical fibers is configured to transmit a pattern of light towards the surface of the aircraft and the pattern of light is configured to cause sound waves in the aircraft when the pattern of light encounters the aircraft. The second array of optical fibers is associated with the sensor structure. The second array of optical fibers is configured to detect a response to the sound waves. The positioning system is configured to determine a location of the inspection vehicle on the aircraft. The support system comprises an elongate member and a line system connected to the elongate member and to the inspection vehicle. The first array of optical fibers and the second array of optical fibers are connected to the elongate member. The support system is configured to support the inspection vehicle in response to an undesired release of the inspection vehicle from the surface of the aircraft. The controller is configured to control movement of the inspection vehicle using the positioning system and control transmission of the pattern of light by the first array of optical fibers and detecting of the response to the sound waves by the second array of optical fibers.

In yet another illustrative embodiment, a method for inspecting a test object using an inspection vehicle is provided. A pattern of light is transmitted from a first array of optical fibers associated with a sensor structure onto a surface of the test object at a location. The pattern of light is configured to cause sound waves in the test object when the pattern of light encounters the test object. A response to the sound waves is detected using a second array of optical fibers associated with the sensor structure. A determination is made as to whether an inconsistency is present in the test object at the location from the response to the sound waves detected using the second array of optical fibers while the inspection vehicle is on the surface of the test object.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 29 is an illustration of an aircraft manufacturing and service method in accordance with an illustrative embodiment; and FIG. 30 is an illustration of an aircraft in which an illustrative embodiment may be implemented.

DETAILED DESCRIPTION

The illustrative embodiments recognize and take into account one or more different considerations. For example, the illustrative embodiments recognize and take into account that one solution may involve using light, such as coherent light, to generate sound waves and detect responses to the sound waves in a test object.

The illustrative embodiments recognize and take into account that a laser ultrasound inspection system may be used to perform inspections of a test object, such as an aircraft part, and in particular, a composite aircraft part. With a laser ultrasound inspection system, physical contact between the sensor and the test object is unnecessary.

The illustrative embodiments recognize and take into account that currently available laser ultrasound inspection systems employ a laser beam that may be scanned across the surface of the test object. The scanning of the laser beam may be performed in a manner such that sound waves travel in a direction into the test object that is substantially perpendicular to the surface of the test object.

The illustrative embodiments recognize and take into account, however, that with currently available laser ultrasound inspection systems, these systems may be more difficult to use than desired. Also, these currently available laser ultrasound inspection systems are often slower than transducer based ultrasound inspection systems when inspecting test objects.

For example, the illustrative embodiments recognize and take into account that scanning a beam across a surface of a test object may take more time than desired. For example, the amount of time needed to scan a test object, such as a wing, may take more time than desired when manufacturing an aircraft.

The illustrative embodiments also recognize and take into account that this type of laser ultrasound inspection system may require placement of the part in an eye-safe room that is configured to avoid undesired exposure by human operators to the laser beam generated by the laser ultrasound inspection system. The illustrative embodiments recognize and take into account that currently available laser ultrasound inspection systems may be more expensive and more complex than desired.

Figure 1:
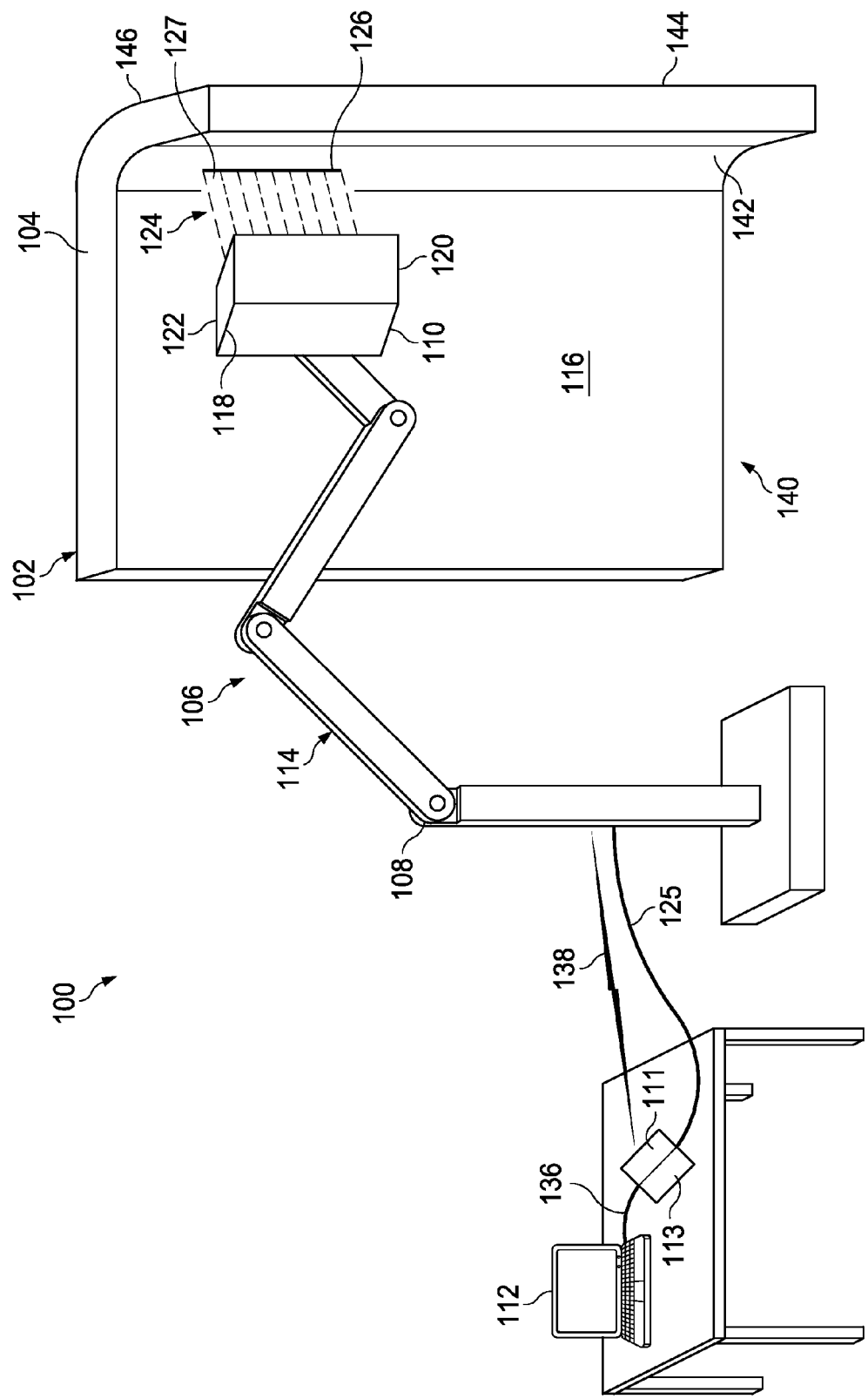
FIG. 1 is an illustration of an inspection environment in accordance with an illustrative embodiment.

With reference now to the figures, and in particular, with reference to FIG. 1, an illustration of an inspection environment is depicted in accordance with an illustrative embodiment. As depicted, inspection environment 100 includes test object 102. In this illustrative example, test object 102 takes the form of composite test object 104. Laser ultrasound inspection system 106 may be used to inspect test object 102.

As depicted, laser ultrasound inspection system 106 comprises robot 108, end effector 110, coherent light source 111, computer 112, and interferometer system 113. Robot 108 takes the form of scanning robot arm 114 in this illustrative example. Robot 108 is configured to move end effector 110 relative to surface 116 of test object 102.

In this illustrative example, end effector 110 may be removably connected to robot 108. As depicted, end effector 110 takes the form of, or includes, sensor 118. Sensor 118 has laser ultrasound source 120 and laser ultrasound detector 122.

Laser ultrasound source 120 is configured to emit coherent light 124 in the form of pattern 126 onto surface 116 of test object 102. In this illustrative example, pattern 126 takes the form of line 127. Coherent light 124 has an energy that is configured to cause sound waves to travel through test object 102.

Coherent light 124 may be transmitted over communications link 125 from coherent light source 111. In this illustrative example, communications link 125 may include optical fibers. Laser ultrasound detector 122 is configured to detect a response to the sound waves generated by coherent light 124 that is emitted onto surface 116 of test object 102 in the form of pattern 126.

Laser ultrasound detector 122 transmits coherent light 124 onto surface 116 in a manner that does not cause sound waves in test object 102 and detects the response to coherent light 124. This response includes information that may be used to identify the response to the sound waves in test object 102. The light in this response is returned to interferometer system 113 over one or more optical fibers in communications link 125.

Computer 112 is configured to control operation of robot 108, coherent light source 111, and other components in laser ultrasound inspection system 106. Computer 112 is connected to coherent light source 111 and interferometer system 113 through communications link 136. Computer 112 may control the operation of coherent light source 111 and may receive data from interferometer system 113 over communications link 136. Computer 112 may communicate with robot 108 using wireless communications link 138.

Further, computer 112 is also configured to analyze the data generated by interferometer system 113 from the light detected by optical fibers in laser ultrasound detector 122. This analysis may include an indication of whether an inconsistency is present in test object 102. Computer 112 may generate a report, an image, and other suitable output based on the inspection of test object 102.

As depicted in FIG. 1, pattern 126 of coherent light 124 is moved across surface 116 of test object 102 to scan test object 102. The scanning using pattern 126 rather than a point from a beam may allow for quicker inspection of test object 102.

In this illustrative example, laser ultrasound inspection system 106 may be especially useful for inspecting non-planar features on surface 116 of test object 102. For example, end effector 110 may be moved over portions of test object 102 in which surface 116 has non-planar features 140.

For example, end effector 110 may be moved over non-planar features 140, such as radius 142 and edge 144. As another example, end effector 110 also may be used to inspect surface 146 of test object 102. This type of inspection may be more easily performed since contact between sensor 118 in end effector 110 is unnecessary when using laser ultrasound source 120 and laser ultrasound detector 122 in sensor 118.

Figure 2:
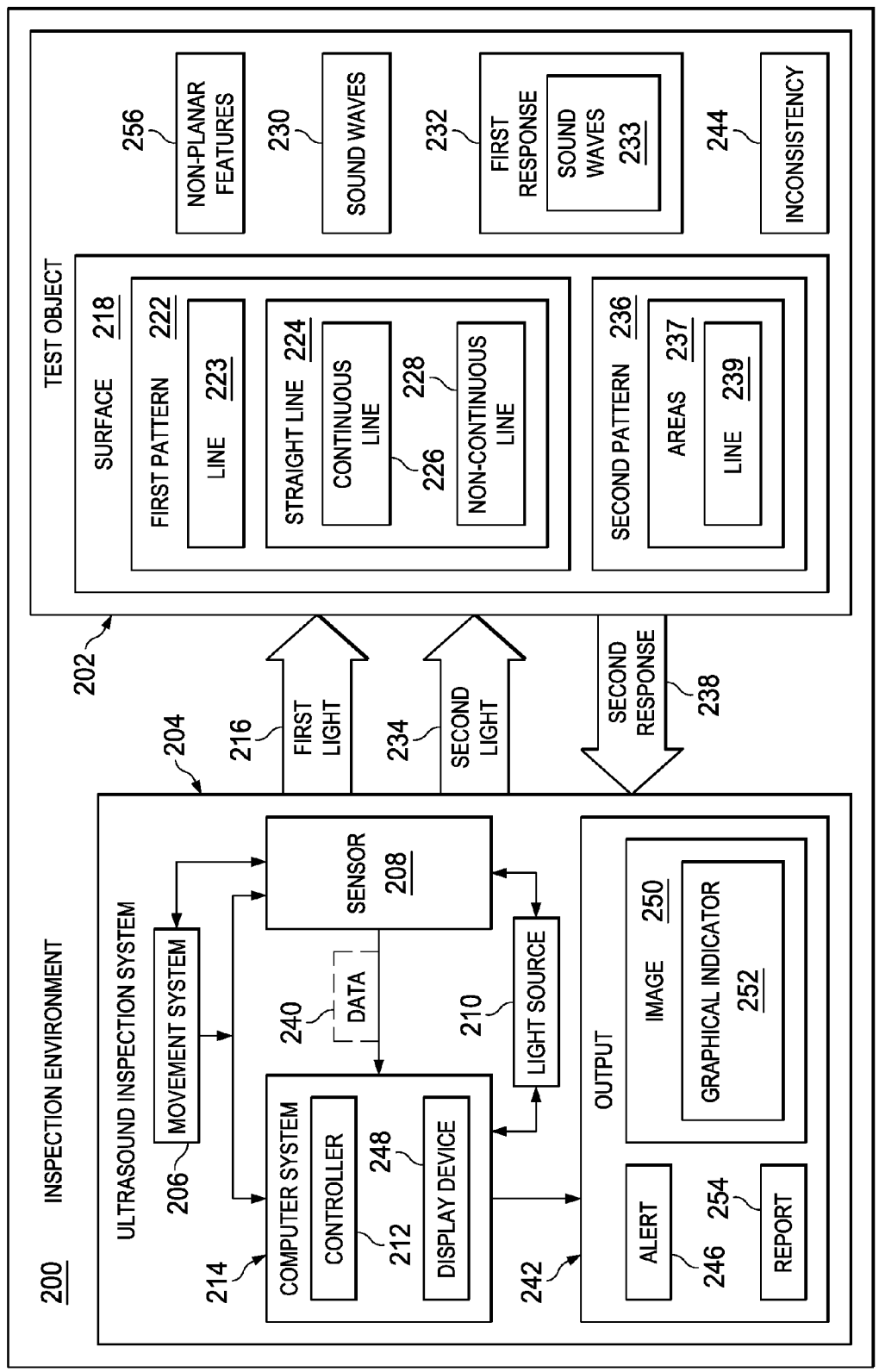
FIG. 2 is an illustration of a block diagram of an inspection environment in accordance with an illustrative embodiment.

Turning now to FIG. 2, an illustration of a block diagram of an inspection environment is depicted in accordance with an illustrative embodiment. Inspection environment 100 in FIG. 1 is one example of a physical implementation of inspection environment 200 shown in block form in this depicted example.

As depicted, inspection environment 200 includes test object 202. Test object 202 may take any number of forms. For example, test object 202 may be a part for an aircraft. Test object 202 may be comprised of different types of materials. For example, test object 202 may be comprised of a number of materials selected from at least one of a composite material, a plastic, a metal, and other suitable types of materials.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and ten of item C; four of item B and seven of item C; and other suitable combinations.

In these illustrative examples, test object 202 may be a composite part for an aircraft selected from one of a panel, a fuselage barrel, a stringer, a spar, a rib, a wing box, a wing, a stabilizer, and other suitable types of parts. Test object 202 may be inspected using ultrasound inspection system 204. As depicted, ultrasound inspection system 204 includes movement system 206, sensor 208, light source 210, and controller 212.

In these illustrative examples, controller 212 controls the operation of ultrasound inspection system 204. Controller 212 may be implemented using hardware, software, or a combination of the two.

In these illustrative examples, controller 212 may be implemented within computer system 214. Computer system 214 may be one or more computers. When more than one computer is present in computer system 214, those computers may be in communication with each other through a communications medium such as a network.

When software is used, the operations performed by the components may be implemented in the program code configured to be run on a processor unit. When hardware is employed, the hardware may include circuits that operate to perform the operations in the components.

In these illustrative examples, the hardware may take the form of a circuit system, an integrated circuit, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. Additionally, the processes may be implemented in organic components integrated with inorganic components and/or may be comprised entirely of organic components excluding a human being. For example, the processes may be implemented as circuits in organic semiconductors.

Movement system 206 is configured to move sensor 208 relative to test object 202. Movement system 206 may be implemented using a number of different types of systems. For example, movement system 206 may be a robot. The robot may be, for example, a robotic arm that may move sensor 208 about a number of axes. Movement system 206 also may be, for example, without limitation, a gantry robot, a hand-operated scanning head, and other suitable types of movement systems.

Sensor 208 is configured to transmit first light 216 onto surface 218 of test object 202. In this illustrative example, first light 216 is transmitted in a manner that forms first pattern 222 on surface 218 of test object 202. In these illustrative examples, first pattern 222 of first light 216 is a plurality of areas on which first light 216 illuminates on surface 218. These areas may be circular, oval, square, oblique, or have some other shape depending on the angle of projection onto the surface. As depicted, first pattern 222 may take the form of line 223.

First pattern 222 is straight line 224 in these illustrative examples. In other words, sensor 208 is configured to transmit first pattern 222 of first light 216 in the form of straight line 224 onto surface 218 of test object 202. In these illustrative examples, first pattern 222 may take the form of continuous line 226 or non-continuous line 228. For example, non-continuous line 228 may be a series of areas. In some illustrative examples, first pattern 222 may have a shape resembling a rectangle or other suitable shape.

First light 216 is configured to generate sound waves 230 within test object 202 when first light 216 encounters test object 202. Sound waves 230 may occur when first light 216 is transmitted onto surface 218 of test object 202. For example, energy in first light 216 may cause thermoelastic expansion in test object 202. The thermoelastic expansion may result in sound waves 230 in test object 202.

In these illustrative examples, sound waves 230 may be ultrasound sound waves. Sound waves 230 may, for example, have a frequency from about 20 kilohertz to about 10 megahertz depending on the particular implementation. The frequency for sound waves 230 may depend on the material used to form test object 202, the pulse width of the laser excitation, and other suitable factors.

Additionally, sensor 208 is configured to detect first response 232 to sound waves 230. First response 232 includes sound waves 233 that may occur as a result of scattering, reflection, modulation, and other changes to sound waves 230 traveling within test object 202. First response 232 is comprised of sound waves 233 that occur in response to sound waves 230. In this illustrative example, first response 232 is detected by sensor 208 transmitting second light 234 onto surface 218 of test object 202 and detecting second response 238 to second light 234.

In one illustrative example, second light 234 also may be transmitted in the form of second pattern 236 onto surface 218 of test object 202. In this illustrative example, second pattern 236 may take the form of areas 237 arranged in line 239. This second pattern, second pattern 236 may substantially line up with the first pattern, first pattern 222, in these illustrative examples.

Second response 238 is second light 234 that has been deflected by first response 232 in this illustrative example. First response 232, caused by sound waves 230 traveling within test object 202, may reach surface 218 and may be detected. The detection of first response 232 may be detected using an interferometer that sends a reference light, such as second light 234 and detects the mechanical vibrations on surface 218 in second response 238.

Sensor 208 sends data 240 to controller 212 when second response 238 is detected. Data 240 is used by controller 212 to generate output 242.

As depicted, output 242 may indicate whether inconsistency 244 is present in test object 202. Inconsistency 244 may be, for example, without limitation, an undesired level of porosity, delamination, and other undesired features or properties in test object 202.

Output 242 may take a number of different forms. For example, output 242 may take the form of alert 246. Alert 246 may indicate whether inconsistency 244 is present. Alert 246 may be displayed on display device 248 within computer system 214.

In another illustrative example, output 242 may be image 250. Image 250 also may be displayed on display device 248. Image 250 may be an image of a portion or all of test object 202 with graphical indicator 252 when inconsistency 244 is present in test object 202. Graphical indicator 252 may be displayed in a location in image 250 corresponding to a location in test object 202 where inconsistency 244 is detected. A location may be described using two-dimensional or three dimensional coordinates. In other illustrative examples, if inconsistency 244 is absent, graphical indicator 252 may be displayed to indicate an absence of inconsistency 244.

As another illustrative example, output 242 may take the form of report 254. Report 254 may identify any inconsistencies in test object 202. Report 254 also may include other information, such as locations of inconsistencies, types of inconsistencies, sizes of inconsistencies, and other suitable types of information. Thus, output 242 may be at least one of alert 246, image 250 with graphical indicator 252, report 254, and other suitable types of output.

In this illustrative example, ultrasound inspection system 204 may be used to inspect portions of test object 202 in which non-planar features 256 may be present. Non-planar features 256 may be present on surface 218 of test object 202. Non-planar features 256 may include, for example, without limitation, at least one of a radius, an edge, a groove, and other non-planar features. In these illustrative examples, the edge may be an edge on a side of test object 202, an edge at a hole formed in test object 202, or some other suitable location for an edge.

Further, with ultrasound inspection system 204, sensor 208 may be positioned more closely to surface 218 of test object 202 as compared to currently used laser ultrasound inspection systems. Changing the position of sensor 208 in ultrasound inspection system 204 may include changing at least one of a location of sensor 208 and an orientation of sensor 208 relative to test object 202.

For example, sensor 208 may be positioned at a location from about 2 millimeters to about 10 millimeters away from surface 218 of test object 202. Of course, other distances may be used when changing the location of sensor 208 depending on the particular implementation.

Further, sensor 208 may be positioned such that the orientation for sensor 208 is in a desired direction. In some illustrative examples, both a location and an orientation for sensor 208 in ultrasound inspection system 204 may be changed when positioning sensor 208.

The positioning of sensor 208 may be located such that issues with eye safety may be reduced. For example, a flexible structure such as a rubber seal or boot may be used with sensor 208 to increase eye safety without using an eye-safe room. Further, with this positioning of sensor 208, the amount of power in first light 216 and second light 234 generated by light source 210 may be reduced. As a result, a need for an eye-safe room for performing inspections of test object 202 may be avoided in some implementations.

Further, with the transmission of first light 216 as first pattern 222 and second light 234 as areas 237 in second pattern 236, the inspection of test object 202 may be performed more quickly by ultrasound inspection system 204 as compared to currently available laser ultrasound inspection systems that use a point of light. Scanning may be reduced because of the length of first pattern 222 and second pattern 236. Instead of scanning point by point, sections may be scanned by moving first pattern 222 of first light 216 and second pattern 236 of second light 234 across surface 218 of test object 202 using ultrasound inspection system 204.

Figure 3:
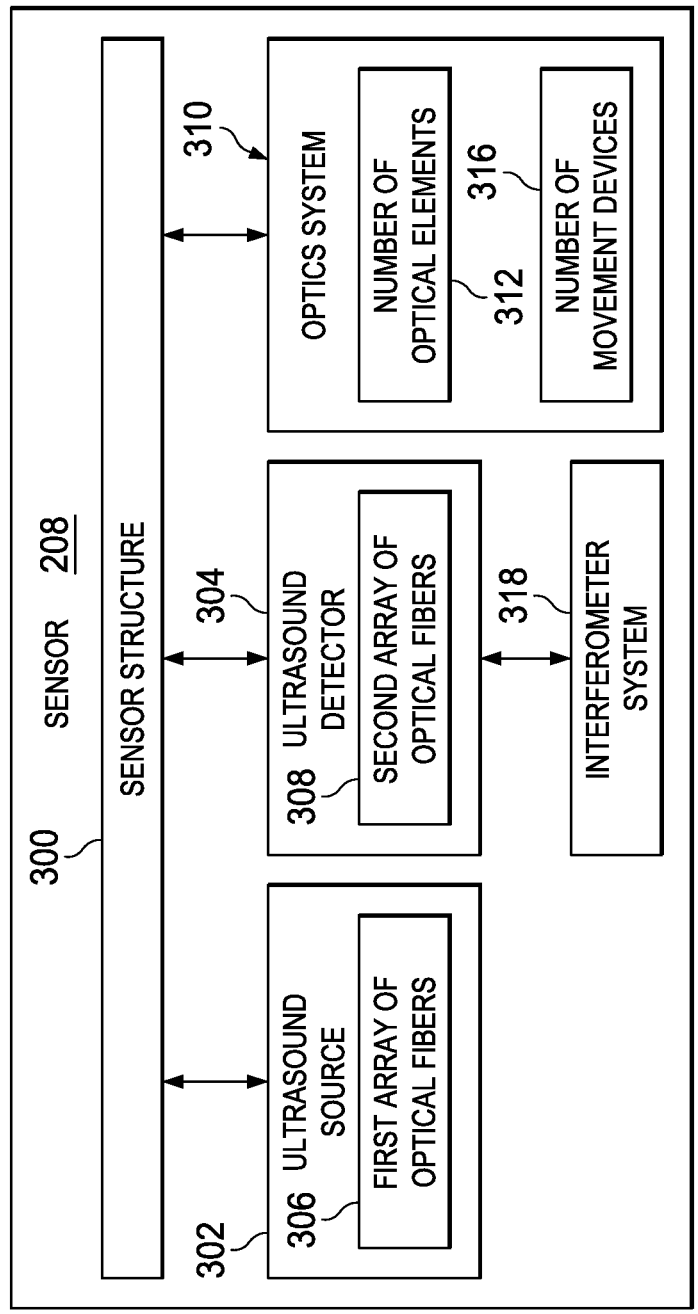
FIG. 3 is an illustration of a block diagram of a sensor in accordance with an illustrative embodiment.

With reference now to FIG. 3, an illustration of a block diagram of a sensor is depicted in accordance with an illustrative embodiment. Examples of components in sensor 208 are shown in this figure.

As depicted, sensor 208 includes sensor structure 300, ultrasound source 302, and ultrasound detector 304. Sensor structure 300 may take a number of different forms. For example, sensor structure 300 may be a housing, a frame, or some other suitable type of physical structure. In one illustrative example, sensor structure 300 may take the form of an end effector configured for attachment to a robot such as end effector 110 for robot 108 in FIG. 1.

In these illustrative examples, ultrasound source 302 and ultrasound detector 304 are associated with sensor structure 300. Ultrasound source 302 is configured to transmit first light 216, while ultrasound detector 304 is configured to detect sound waves 233 in first response 232 in response to sound waves 230.

When one component is "associated" with another component, the association is a physical association in these depicted examples. For example, a first component, ultrasound source 302, may be considered to be associated with a second component, sensor structure 300, by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

Ultrasound source 302 is comprised of first array of optical fibers 306. First array of optical fibers 306 is configured to receive first light 216 from light source 210 and transmit first light 216 in the form of first pattern 222 onto surface 218 of test object 202. First light 216 from first array of optical fibers 306 is configured to cause excitation in test object 202. In other words, first light 216 from first array of optical fibers 306 is configured to generate sound waves 230 within test object 202.

As depicted, ultrasound detector 304 is comprised of second array of optical fibers 308. Second array of optical fibers 308 is configured to transmit second light 234 and detect second response 238 to second light 234. Second light 234 is not configured to generate sound waves 230 within test object 202. Instead, second light 234 is configured to reflect, scatter, or otherwise interact with surface 218 of test object 202, the air around surface 218 of test object 202, or both in a manner such that the portion of second light 234 that is received by second array of optical fibers 308 may be affected by sound waves 233 in first response 232 that reach surface 218 of test object 202.

In some illustrative examples, overlap is present in the time between the two patterns of light, first pattern 222 and second pattern 236, being transmitted onto surface 218. With this overlap, second array of optical fibers 308 may be used to monitor for first response 232 at the same time or prior to the generation of sound waves 230.

In other illustrative examples, each optical fiber in first array of optical fibers 306 may transmit first light 216 sequentially rather than at the same time. Additionally, groupings of optical fibers in first array of optical fibers 306 may sequentially transmit first light 216. Second light 234 may be transmitted in a similar fashion by second array of optical fibers 308. In still other illustrative examples, first light 216 may be transmitted using different phases, wavelengths, or both in addition to transmitting first light 216 through optical fibers in first array of optical fibers 306, second array of optical fibers 308, or both at different times.

Mechanisms such as delay lines and delay circuits separate lasers in light source 210. These mechanisms may reduce cross-talk in the optical fibers that results in first light 216 in first array of optical fibers 306 and second light 234 in second array of optical fibers 308 from exiting one optical fiber and entering another optical fiber. In other words, different phases, wavelengths, timings or some combination thereof may be used to reduce cross-talk between optical fibers within first array of optical fibers 306 and second array of optical fibers 308.

In these illustrative examples, sensor 208 also may include optics system 310. Optics system 310 is associated with sensor structure 300. As depicted, optics system 310 is a hardware system and may include components such as number of optical elements 312, number of movement devices 316, and other suitable components.

Optics system 310 is configured to direct the transmission of first light 216 and second light 234 to surface 218 of test object 202. Further, optics system 310 also may direct second response 238 to second array of optical fibers 308.

Number of optical elements 312 is configured to modify the transmission of first light 216 and second light 234 in these illustrative examples. Number of optical elements 312 may include at least one of a lens, a mirror, a diffractive optical element, a polarizer, a wave plate, a periodically-poled Lithium niobate crystal, or other suitable optical elements.

For example, number of optical elements 312 may be configured to shape first light 216 transmitted from first array of optical fibers 306 to form first pattern 222. In a similar fashion, number of optical elements 312 may be used to shape second light 234 transmitted from second array of optical fibers 308 to form areas 237 in second pattern 236 with a desired size. Number of optical elements 312 also may be used to change the polarization of first light 216 and second light 234, the color of first light 216 and second light 234, and other parameters of first light 216 and second light 234.

In these illustrative examples, number of movement devices 316 may be used to move one or more of number of optical elements 312 to cause movement of first pattern 222 of first light 216 and second pattern 236 of second light 234. This movement may occur without moving sensor structure 300 in this illustrative example. Number of movement devices 316 may include, for example, at least one of a motor, an actuator, and other suitable types of devices that may be configured to move number of optical elements 312.

Sensor 208 also may include interferometer system 318. Interferometer system 318 is a hardware device and is configured to identify information from the light forming second response 238. Interferometer system 318 may include one or more interferometers in these illustrative examples. The information identified by interferometer system 318 may include, for example, displacements, deflections, surface velocity, and other information that may be used to identify second response 238 as detected by second array of optical fibers 308 receiving the light in second response 238.

In some illustrative examples, interferometer system 318 may be considered part of ultrasound detector 304 even though interferometer system 318 may not be located in sensor structure 300. Interferometer system 318 may be associated with optics system 310 or may be in a separate location.

Figure 4:
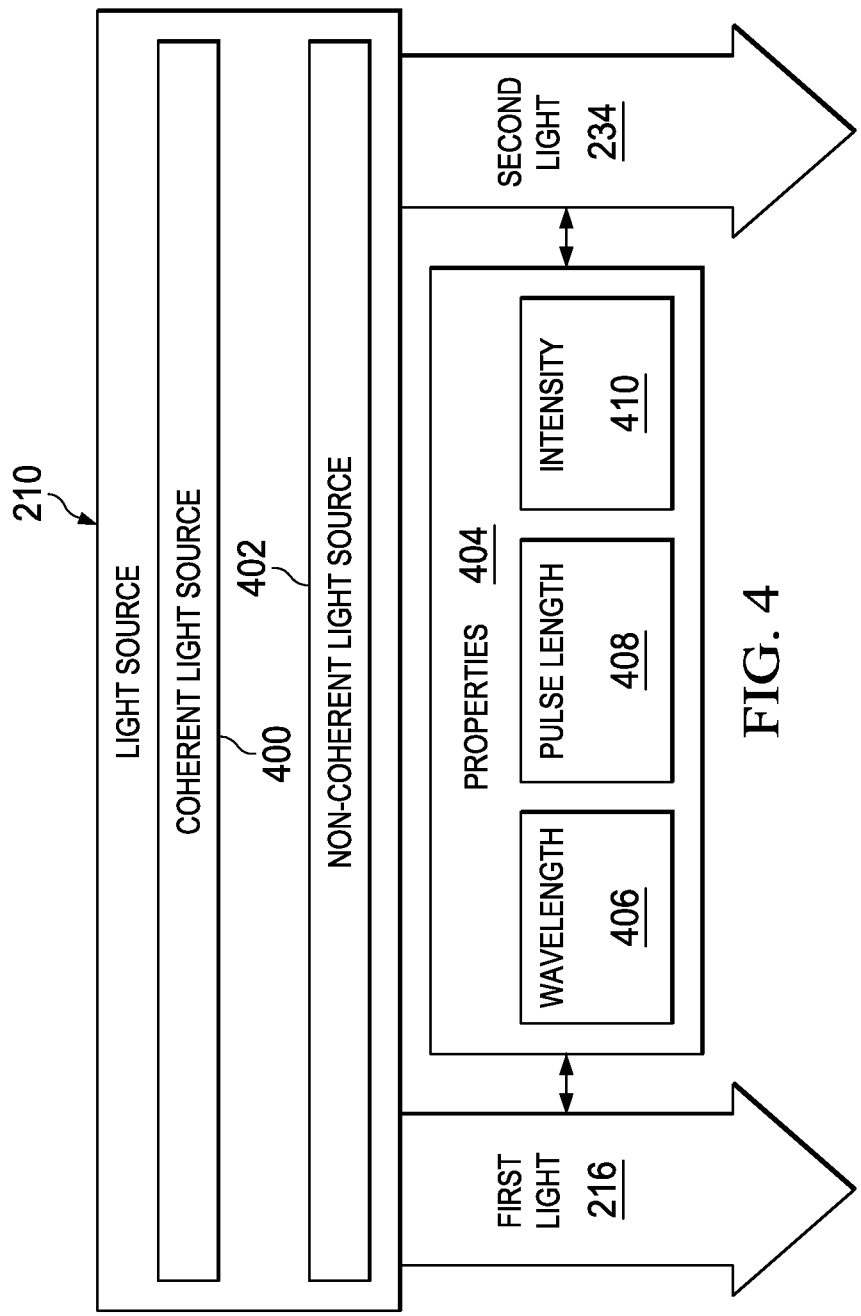
FIG. 4 is an illustration of a block diagram of a light source in accordance with an illustrative embodiment.

Turning now to FIG. 4, an illustration of a block diagram of a light source is depicted in accordance with an illustrative embodiment. In these illustrative examples, light source 210 may be, for example, at least one of coherent light source 400 and non-coherent light source 402. Coherent light source 400 may be, for example, a laser, an array of laser diodes, or some other suitable source of coherent light. Non-coherent light source 402 may be, for example, an array of light emitting diodes, xenon light, or some other suitable source of non-coherent light.

As depicted, light source 210 is configured to generate first light 216 and second light 234 with properties 404. Properties 404 include wavelength 406, pulse length 408, and intensity 410. Properties 404 may be different for first light 216 and second light 234

Wavelength 406 may be selected based on the material forming test object 202, the thickness of test object 202, and other suitable factors. Wavelength 406 may be selected for first light 216 in a manner that increases absorption of energy from first light 216 when first light 216 and second light 234 are transmitted onto surface 218 of test object 202. For example, when test object 202 is comprised of one or more composite materials, wavelength 406 selected for first light 216 may be from about 300 millimeters to about 30,000 millimeters. Wavelength 406 may be the same for generating both sound waves 230 and first response 232.

Pulse length 408 may be selected for first light 216 to generate a desired frequency for sound waves 230. For example, a pulse duration of about 1 nanosecond to about 200 nanoseconds may be used. Pulse length 408 may be selected to have a duration of about 50 microseconds to about 100 microseconds for second light 234 that is used to detect sound waves 233 in first response 232.

Intensity 410 is selected based on the amount of energy that is desired to be transmitted into test object 202 by first light 216 encountering surface 218 of test object 202. Intensity 410 may be selected for first light 216 to provide a desired level of sound waves 230 when first light 216 is transmitted onto surface 218 of test object 202. Intensity 410 may be selected for first light 216 and second light 234 to reduce or avoid damage to surface 218 of test object 202. Of course, the intensity also may vary depending on the values selected for pulse length 408.

Although specific values have been specified for properties 404, these values are only presented for purposes of illustration and not meant to limit other values that may be used. The selection of properties 404 may vary depending on light source 210, materials in test object 202, and other factors.

The illustration of inspection environment 200 and the different components in inspection environment 200 in FIGS. 2-4 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, in some illustrative embodiments, ultrasound source 302 and ultrasound detector 304 may be placed in separate sensor structures. In other illustrative examples, sensor 208 may be moved by a human operator rather than a robot or other type of machine. In other words, movement system 206 may take the form of a human operator.

In still another illustrative example, optics system 310 may be implemented using more than one block. For example, optics system 310 may be part of ultrasound source 302, ultrasound detector 304, or both rather than being a separate block.

In another illustrative example, test object 202 may be an object for other types of platforms other than an aircraft. The platform in which the test object may be located may be, for example, a mobile platform, a stationary platform, a land-based structure, an aquatic-based structure, and a space-based structure. More specifically, the platform, may be a surface ship, a tank, a personnel carrier, a train, a spacecraft, a space station, a satellite, a submarine, an automobile, a power plant, a bridge, a dam, a manufacturing facility, a roadway, a building, and other suitable platforms.

Figure 5:
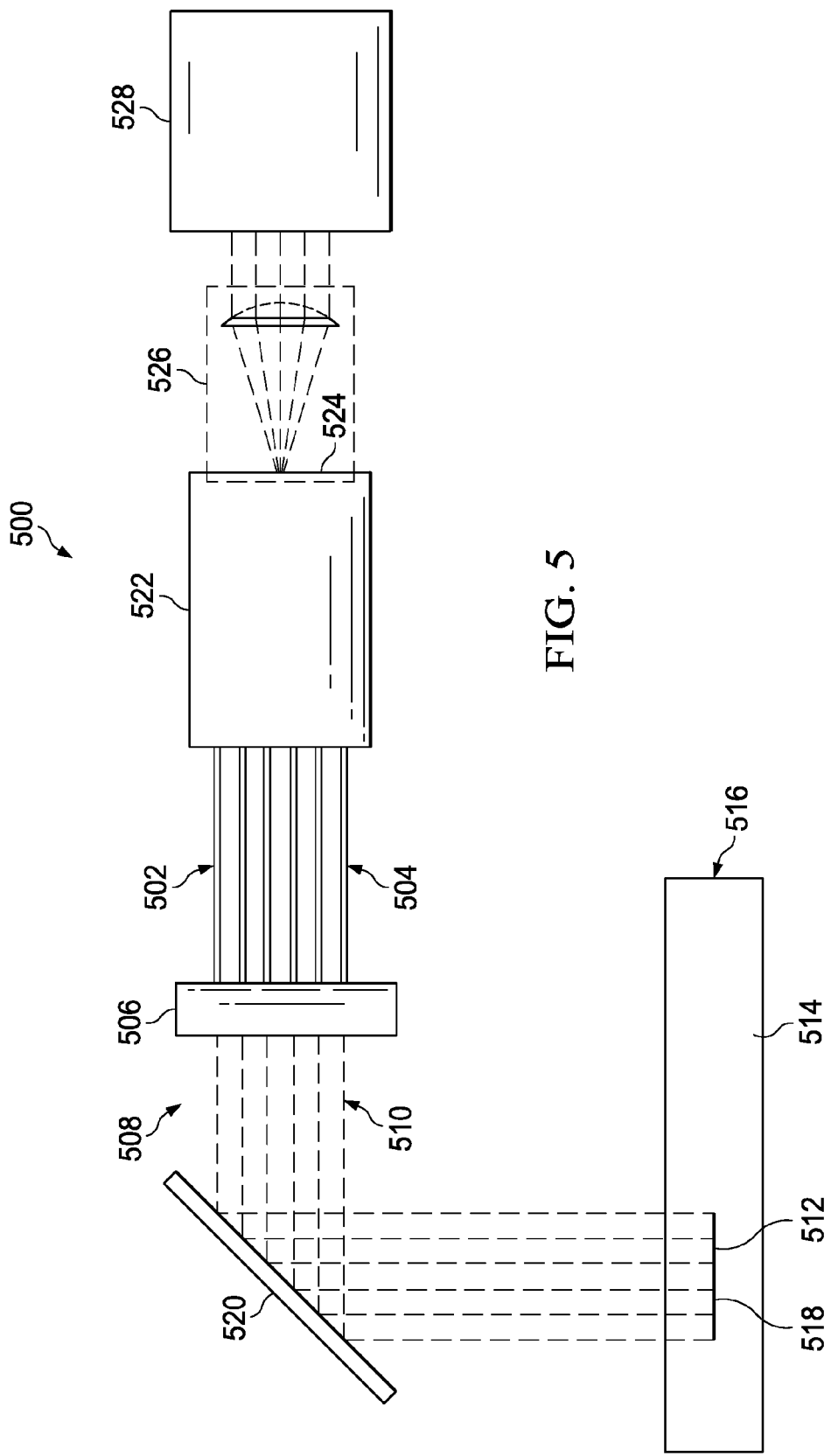
FIG. 5 is an illustration of an ultrasound source in accordance with an illustrative embodiment.

Turning now to FIG. 5, an illustration of an ultrasound source is depicted in accordance with an illustrative embodiment. Ultrasound source 500 is an example of one implementation for ultrasound source 302 shown in block form in FIG. 3.

In this illustrative example, optical fibers 502 are arranged in array 504. Optical fibers 502 may be implemented using any type of optical fiber that is configured to carry light within the optical fibers.

In this illustrative example, six optical fibers are present in optical fibers 502. Array 504 is a 1×6 array in this illustrative example. Of course, other numbers of optical fibers and other types of arrays may be used. For example, optical fibers 502 may include three fibers, fifteen fibers, twenty-seven fibers, or some other suitable number of fibers. Further, in some illustrative examples, the array may have two or more rows instead of a single row of optical fibers.

Ultrasound source 500 also includes cylinder lens 506. Cylinder lens 506 is configured to cause light 508 transmitted by array 504 of optical fibers 502 to form beams 510 which has a linear shape. Cylinder lens 506 is configured to shape light 508. In particular, cylinder lens 506 is configured to cause light 508 to form pattern 512 on surface 514 of test object 516 as a continuous line. In this illustrative example, cylinder lens 506 may function to cause pattern 512 of light 508 to have an intensity with a Gaussian profile. In this illustrative example, the Gaussian profile is in an X and Y direction relative to a plane on surface 514 of test object 516.

In these illustrative examples, if optical fibers 502 in array 504 are spaced far enough apart, then a pattern of individual areas is formed on surface 514 of test object 516. Each area is "approximately a Gaussian profile" in both X and Y directions. Cylinder lens 506 causes the Gaussian profiles to be different in the X and Y directions.

In particular, cylinder lens 506 is configured to reduce divergence in a manner such that beams 510 are focused in one direction and form pattern 512 when reaching surface 514 of test object 516. In these illustrative examples, pattern 512 takes the form of line 518. Line 518 may be formed from the intersection or overlapping of beams 510 on surface 514 of test object 516. Without cylinder lens 506, the divergence of beams 510 may be in two dimensions resulting in an oval or circular shape rather than a line.

In this example, mirror 520 is an example of a component that may be used to implement optics system 310 in FIG. 3. Mirror 520 is configured to manage the direction in which beams 510 of light 508 travel to reach surface 514 of test object 516.

As depicted, optical fibers 502 may be grouped and covered to form fiber bundle 522. In this illustrative example, end 524 of fiber bundle 522 is connected to collimator 526.

Collimator 526 is connected to laser 528. Laser 528 is the source of light 508. As depicted, light 508 is sent through collimator 526. Collimator 526 is configured to make light 508 coherent in these illustrative examples.

Figure 6:
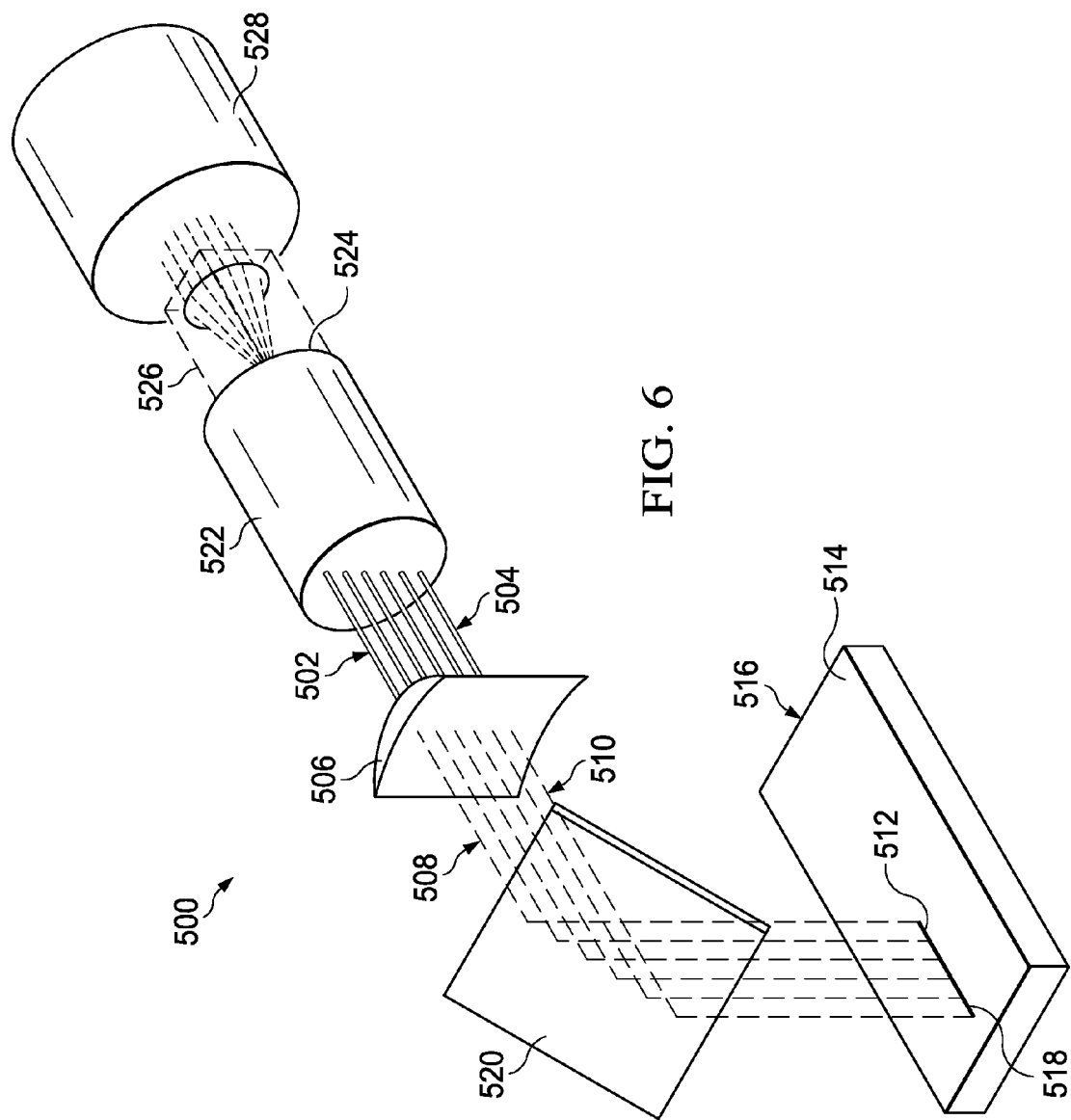
FIG. 6 is an illustration of an ultrasound source in accordance with an illustrative embodiment.

Turning now to FIG. 6, an illustration of an ultrasound source is depicted in accordance with an illustrative embodiment. In this depicted example, ultrasound source 500 is shown in a perspective view.

Figure 7:
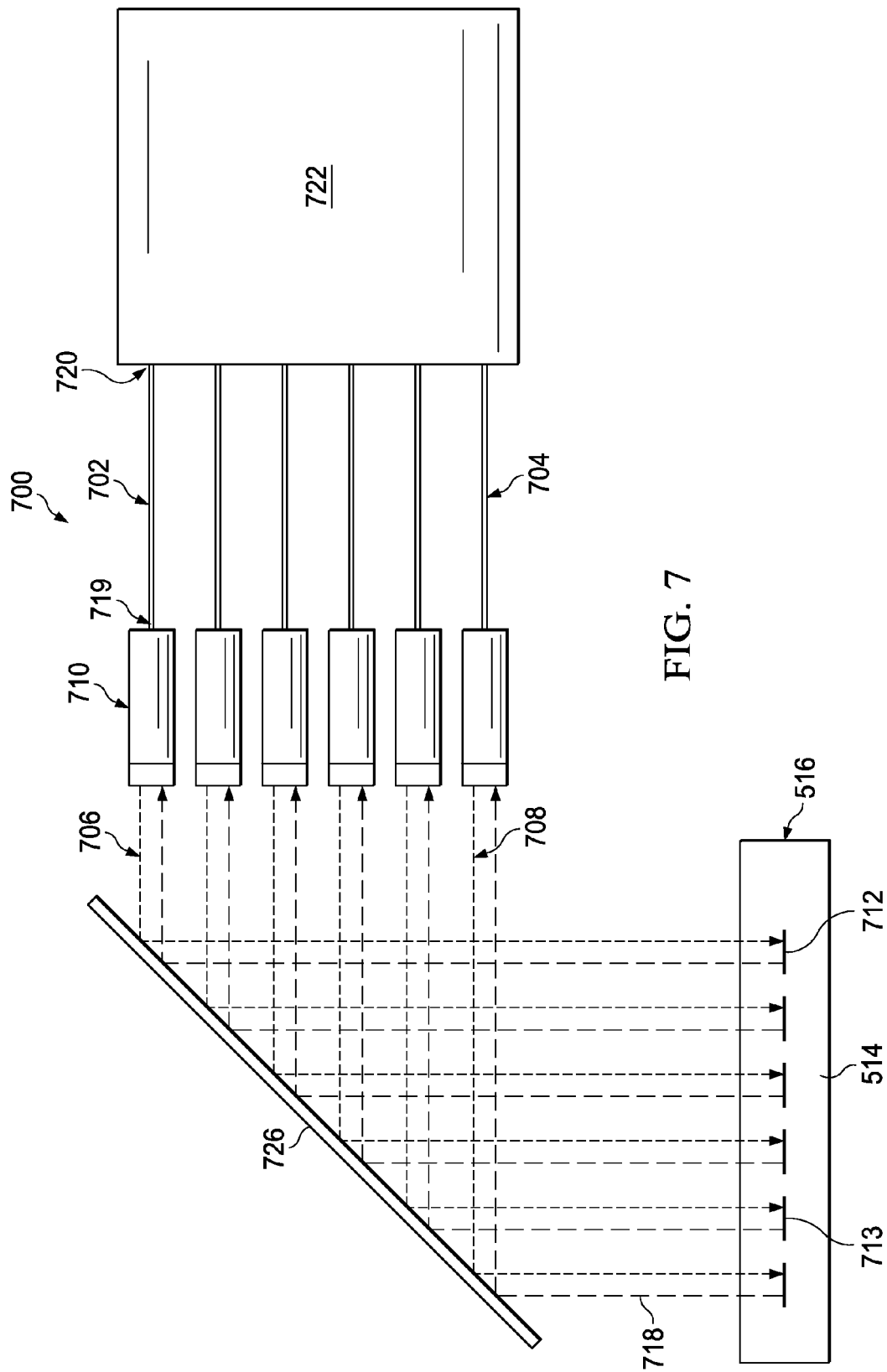
FIG. 7 is an illustration of an ultrasound detector in accordance with an illustrative embodiment.

Turning now to FIG. 7, an illustration of an ultrasound detector is depicted in accordance with an illustrative embodiment. Ultrasound detector 700 is an example of one implementation for ultrasound detector 304 shown in block form in FIG. 3. As depicted, ultrasound detector 700 includes optical fibers 702. Optical fibers 702 are arranged as array 704. Array 704 of optical fibers 702 is configured to emit beams 706 of light 708.

In this illustrative example, six optical fibers are present in optical fibers 702. Additionally, array 704 is a 1×6 array. Of course, other numbers of optical fibers and other configurations for array 704 may be present depending on the particular implementation.

In this illustrative example, ultrasound detector 700 also includes collimators 710. As depicted, each optical fiber in optical fibers 702 is associated with a collimator in collimators 710.

In these illustrative examples, collimators 710 may be implemented using different types of collimators. For example, without limitation, collimators 710 may be selected from at least one of an aspherical lens collimator, a spherical lens collimator, a grin lens collimator, or some other suitable type of collimator. Collimators 710 are used to change light 708 into coherent light in these illustrative examples.

Light 708 is comprised of light waves that are in phase with each other. With light 708, the phases of the electromagnetic waves at each point on a line normal to the direction of which beams 706 are traveling is identical.

In this illustrative example, beams 706 of light 708 form pattern 712 on surface 514 of test object 516. In this illustrative example, pattern 712 is in the form of line 713. Line 713 of pattern 712 is a non-continuous line in this illustrative example. In other illustrative examples, line 713 of pattern 712 may be a continuous line.

In this illustrative example, light 708 transmitted by optical fibers 702 onto surface 514 of test object 516 results in response 718. Response 718 is comprised of light. The light in response 718 is caused by interaction with surface 514. For example, light 708 may reflect, scatter, or reflect and scatter off of surface 514.

Response 718 is detected at end 719 of optical fibers 702 and may be transmitted through optical fibers 702 in a direction opposite to the transmission of light 708. In this illustrative example, end 720 of optical fibers 702 in array 704 are connected to interferometer system 722. Interferometer system 722 is the source of light 708 and receives response 718.

In this illustrative example, mirror 726 is an example of a component that may be used to implement optics system 310 in FIG. 3. Mirror 726 is configured to control the direction in which light 708 and response 718 travel.

Figure 8:
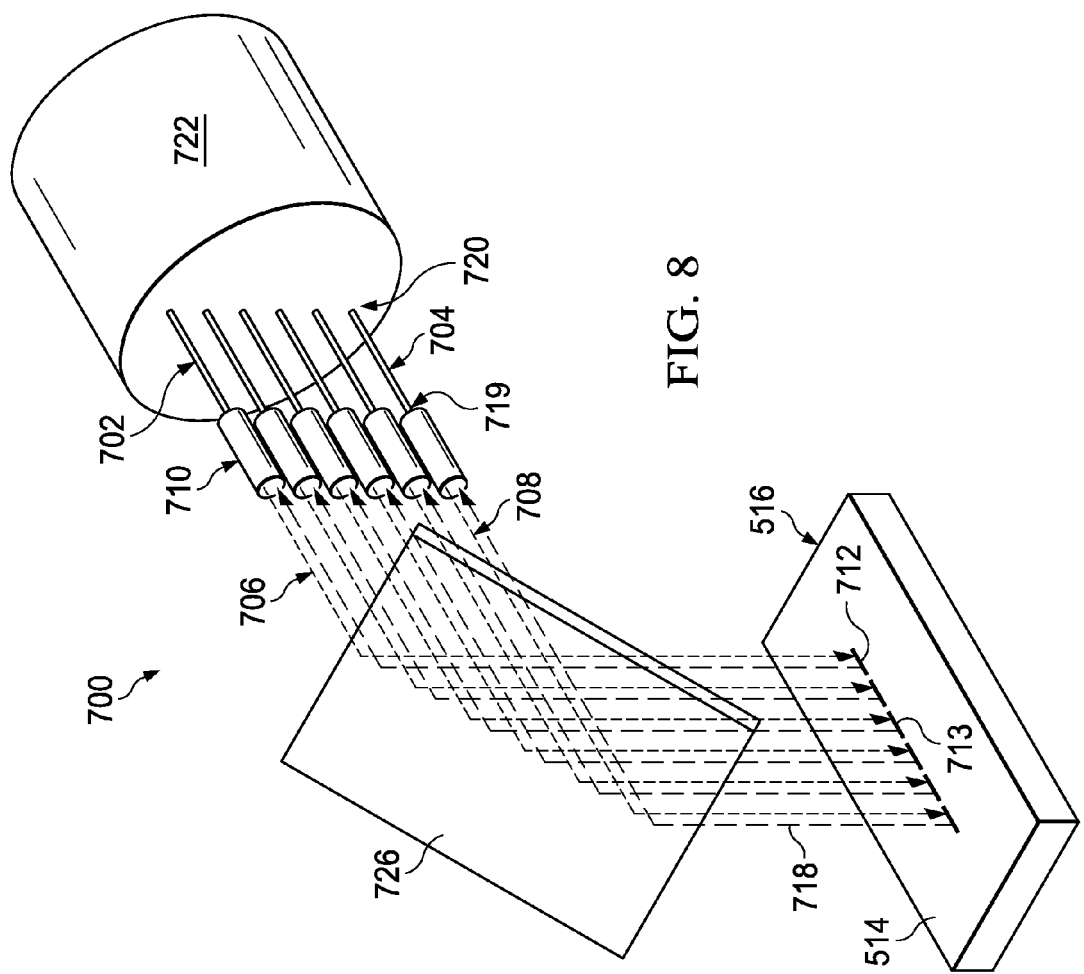
FIG. 8 is an illustration of an ultrasound detector in accordance with an illustrative embodiment.

Turning now to FIG. 8, an illustration of an ultrasound detector is depicted in accordance with an illustrative embodiment. In this illustrative example, a perspective view of ultrasound detector 700 is shown.

Figure 9:
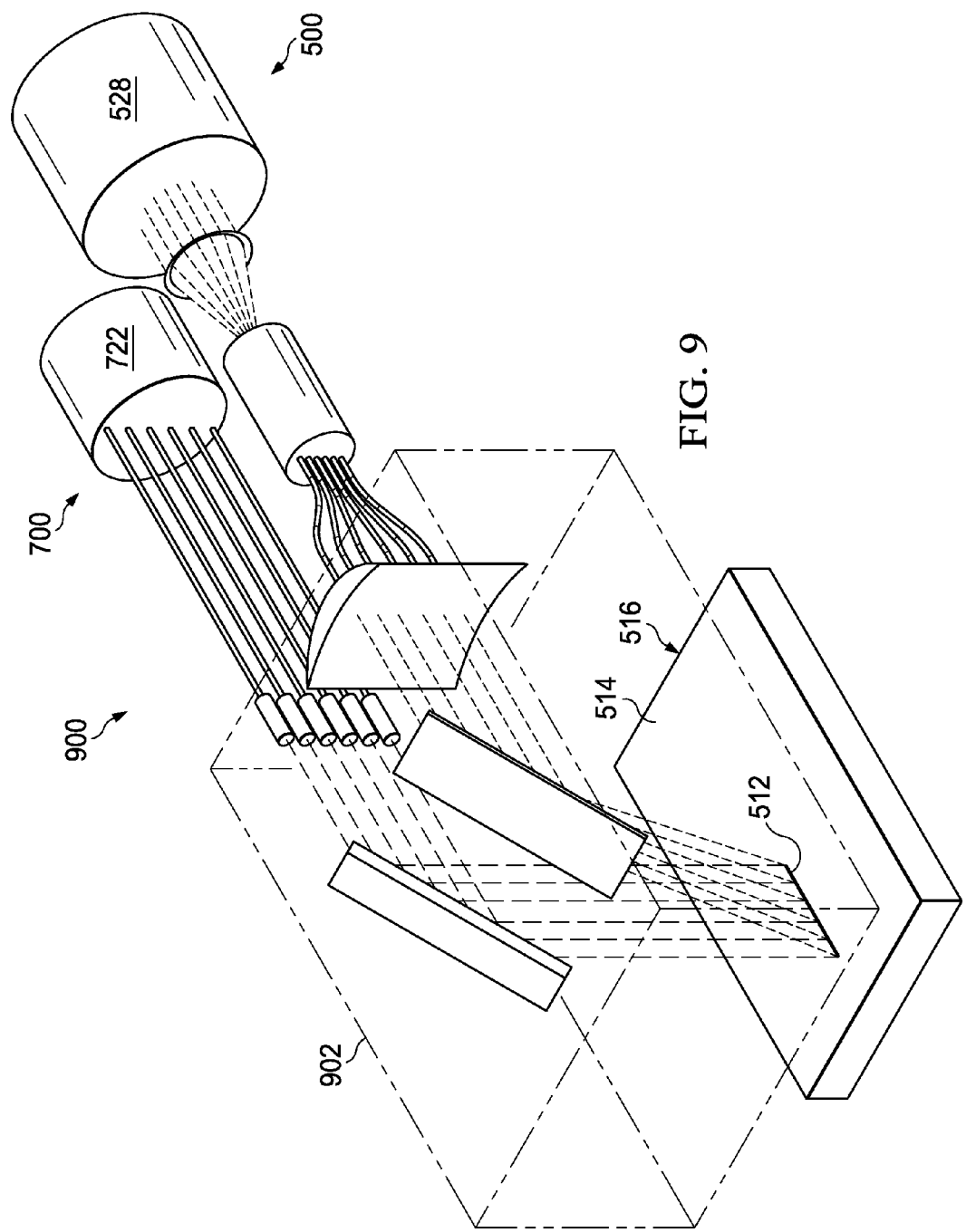
FIG. 9 is an illustration of an ultrasound inspection system in accordance with an illustrative embodiment.

Turning now to FIG. 9, an illustration of an ultrasound inspection system is depicted in accordance with an illustrative embodiment. In this depicted example, a perspective view of ultrasound inspection system 900 is shown. In this example, ultrasound inspection system 900 includes ultrasound source 500, ultrasound detector 700, and sensor structure 902.

Sensor structure 902 takes the form of a housing for an end effector in this illustrative example. As depicted, components for ultrasound source 500 and ultrasound detector 700 are located inside of sensor structure 902 but not seen in this example.

Figure 10:
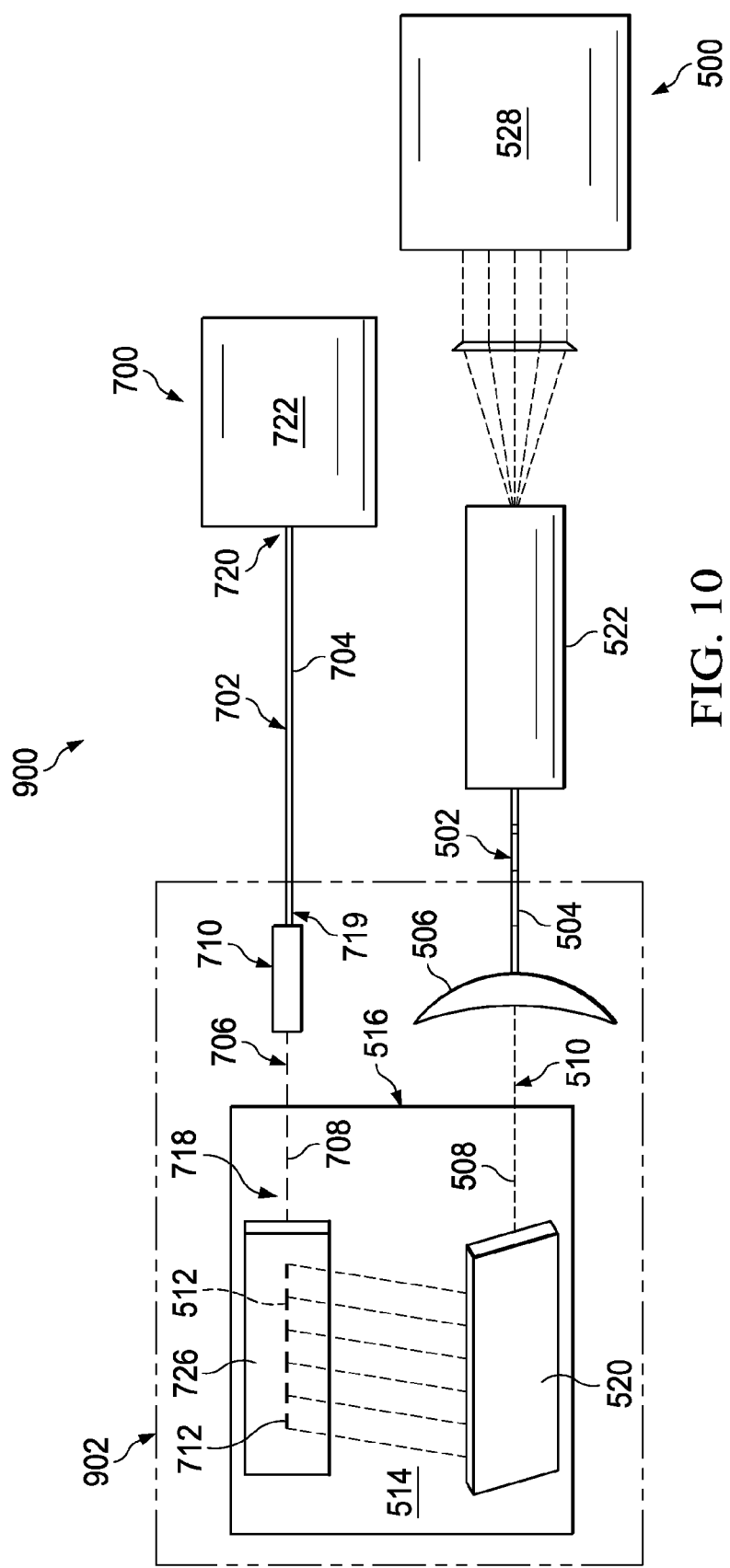
FIG. 10 is an illustration of a top view of an ultrasound inspection system in accordance with an illustrative embodiment.

Turning next to FIG. 10, an illustration of a top view of an ultrasound inspection system is depicted in accordance with an illustrative embodiment. In this view, sensor structure 902 may be positioned over surface 514 of test object 516 to perform inspection of test object 516.

In this illustrative example, pattern 512 and pattern 712 are aligned with each other on surface 514 of test object 516. In other words, pattern 512 is transmitted onto the same location as pattern 712 in this illustrative example. As a result, these two patterns substantially overlap each other.

Pattern 512 of light 508 is configured to generate sound waves within test object 516. Responses to sound waves may cause vibrations in surface 514 of test object 516. Pattern 712 of light 708 is configured to generate response 718 which includes variations or changes in surface 514 due to vibrations caused by the response to the sound waves. Response 718 is detected by optical fibers 702.

In these illustrative examples, laser 528 generates light 508. Light 508 is collimated by collimator 526 in this illustrative example. This collimated light is then transmitted through optical fibers 502 in the manner described with respect to FIG. 5 and FIG. 6.

In these illustrative examples, light 708 may be generated by interferometer system 722. Response 718 to light 708 may travel through optical fibers 702 back to interferometer system 722. Interferometer system 722 may use response 718 to generate data used to determine whether an inconsistency is present in test object 516.

Figure 11:
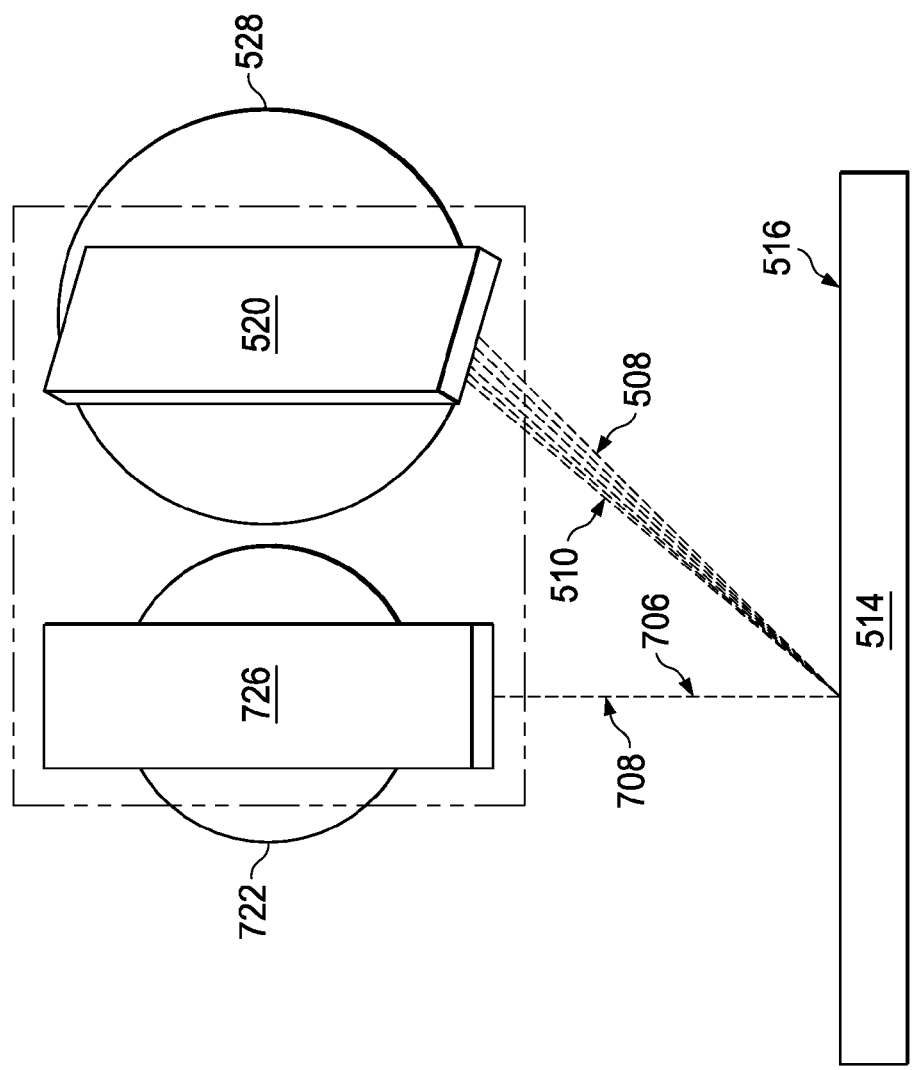
FIG. 11 is an illustration of a front view of an ultrasound inspection system in accordance with an illustrative embodiment.

Turning now to FIG. 11, an illustration of a front view of an ultrasound inspection system is depicted in accordance with an illustrative embodiment. In this illustrative example, another cross-sectional view of ultrasound inspection system 900 is shown.

Figure 12:
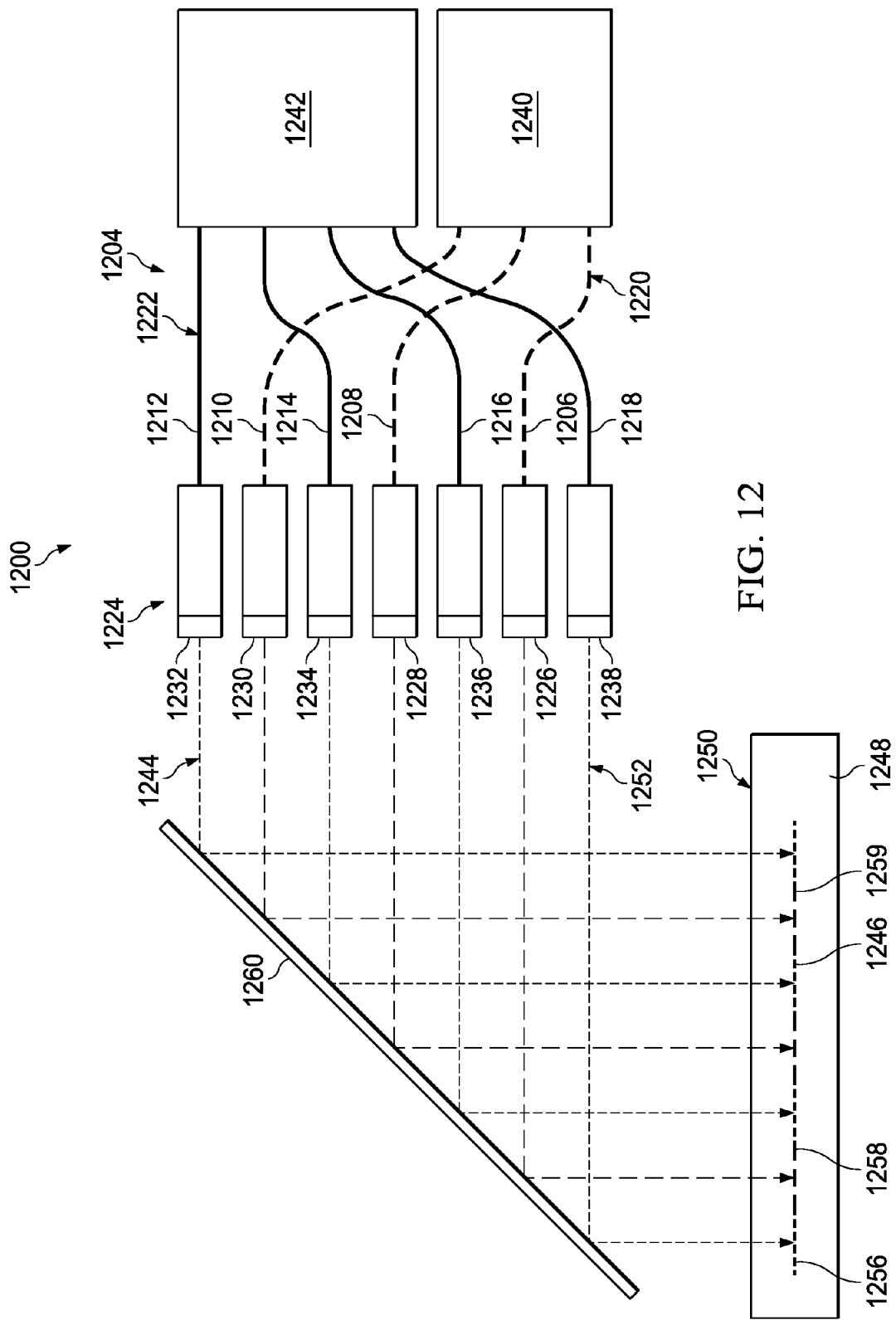
FIG. 12 is another illustration of an ultrasound inspection system in accordance with an illustrative embodiment.

Turning now to FIG. 12, another illustration of an ultrasound inspection system is depicted in accordance with an illustrative embodiment. As depicted, ultrasound inspection system 1200 is another example of an implementation for ultrasound inspection system 204 shown in block form in FIG. 2.

In this illustrative example, ultrasound inspection system 1200 includes optical fibers 1204. Optical fibers 1204 comprise optical fibers 1206, 1208, 1210, 1212, 1214, 1216, and 1218. Optical fibers 1206, 1208, and 1210 form first array of optical fibers 1220. Optical fibers 1212, 1214, 1216, and 1218 form second array of optical fibers 1222.

In this illustrative example, optical fibers 1204 are associated with collimators 1224. Collimators 1224 comprise collimators 1226, 1228, 1230, 1232, 1234, 1236, and 1238. Collimators 1226, 1228, and 1230 are associated with optical fibers 1206, 1208, and 1210, respectively. Collimators 1232, 1234, 1236, and 1238 are associated with optical fibers 1212, 1214, 1216, and 1218, respectively. In this illustrative example, optical fibers 1206, 1208, and 1210, in first array of optical fibers 1220, are interspersed with optical fibers 1212, 1214, 1216, and 1218 in second array of optical fibers 1222.

In this illustrative example, first array of optical fibers 1220 is connected to laser 1240. Second array of optical fibers 1222 are connected to interferometer system 1242. In this illustrative example, light 1244 from first array of optical fibers 1220 is emitted in the form of pattern 1246 onto surface 1248 of test object 1250. Light 1252 from second array of optical fibers 1222 forms pattern 1256 on surface 1248 of test object 1250.

In this illustrative example, pattern 1246 of light 1244 and pattern 1256 of light 1252 are non-continuous lines. As depicted, pattern 1246 of light 1244 takes the form of line 1258, and pattern 1256 of light 1252 takes the form of line 1259. These two patterns of light encounter surface 1248 at substantially the same location. In other words, these two patterns of light would overlap each other if transmitted at the same time.

In this illustrative example, mirror 1260 is an example of an optical system that may be used to control the direction in which light 1244 and light 1252 travel. Mirror 1260 may be one implementation for optics system 310 shown in block form in FIG. 3.

Figure 13:
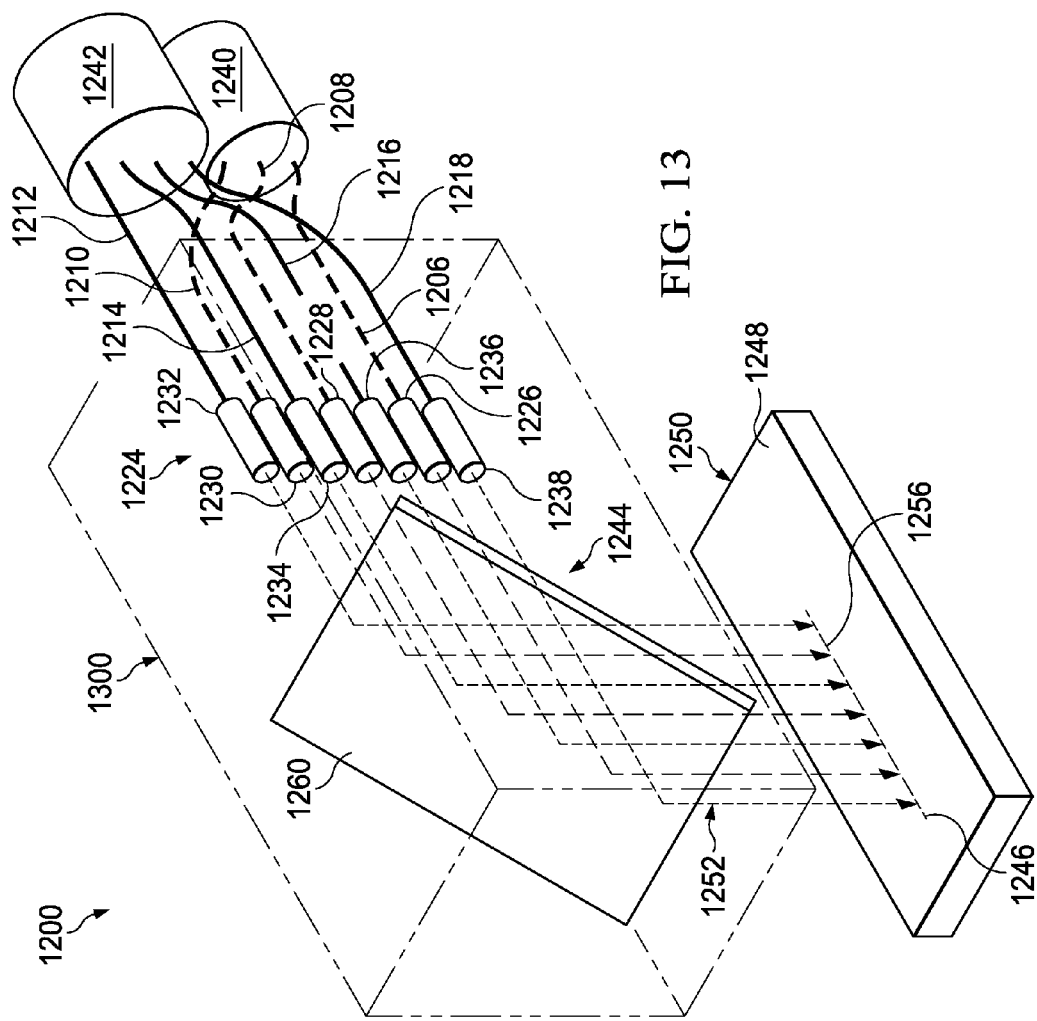
FIG. 13 is an illustration of a perspective view of an ultrasound inspection system in accordance with an illustrative embodiment.

Turning now to FIG. 13, an illustration of a perspective view of an ultrasound inspection system is depicted in accordance with an illustrative embodiment. In this perspective view, sensor structure 1300 is shown in phantom with some of the components in ultrasound inspection system 1200 from FIG. 12 located within sensor structure 1300.

The illustration of the different embodiments of an ultrasound inspection system in FIGS. 5-13 is not meant to imply limitations in the way in which other illustrative embodiments may be implemented. For example, other numbers of optical fibers may be used other than those depicted. In still other illustrative examples, the light source for the first array of optical fibers and the second array of optical fibers may be a single light source.

In yet another illustrative example, a diffractive diffuser may be used to shape light 508 emitted from array 504 of optical fibers 502. The diffractive diffuser may be used in addition to or in place of cylinder lens 506.

The different components shown in FIG. 1 and FIGS. 5-13 may be combined with components in FIGS. 2-4, used with components in FIGS. 2-4, or a combination of the two. Additionally, some of the components in FIG. 1 and FIGS. 5-13 may be illustrative examples of how components shown in block form in FIGS. 2-4 can be implemented as physical structures.

The different illustrative embodiments also recognize and take into account that non-destructive evaluation testing, such as ultrasound inspection, may be performed in an automated manner. The illustrative embodiments recognize and take into account that scanning robot arm 114 in FIG. 1 is only one manner in which ultrasound inspection may be performed using an ultrasound inspection system.

Other types of devices also may be used during an ultrasound inspection. For example, a vehicle with sensor 208 in FIG. 2 may be placed on a test object and moved along the surface of the test object to perform the ultrasound inspection.

Figure 14:
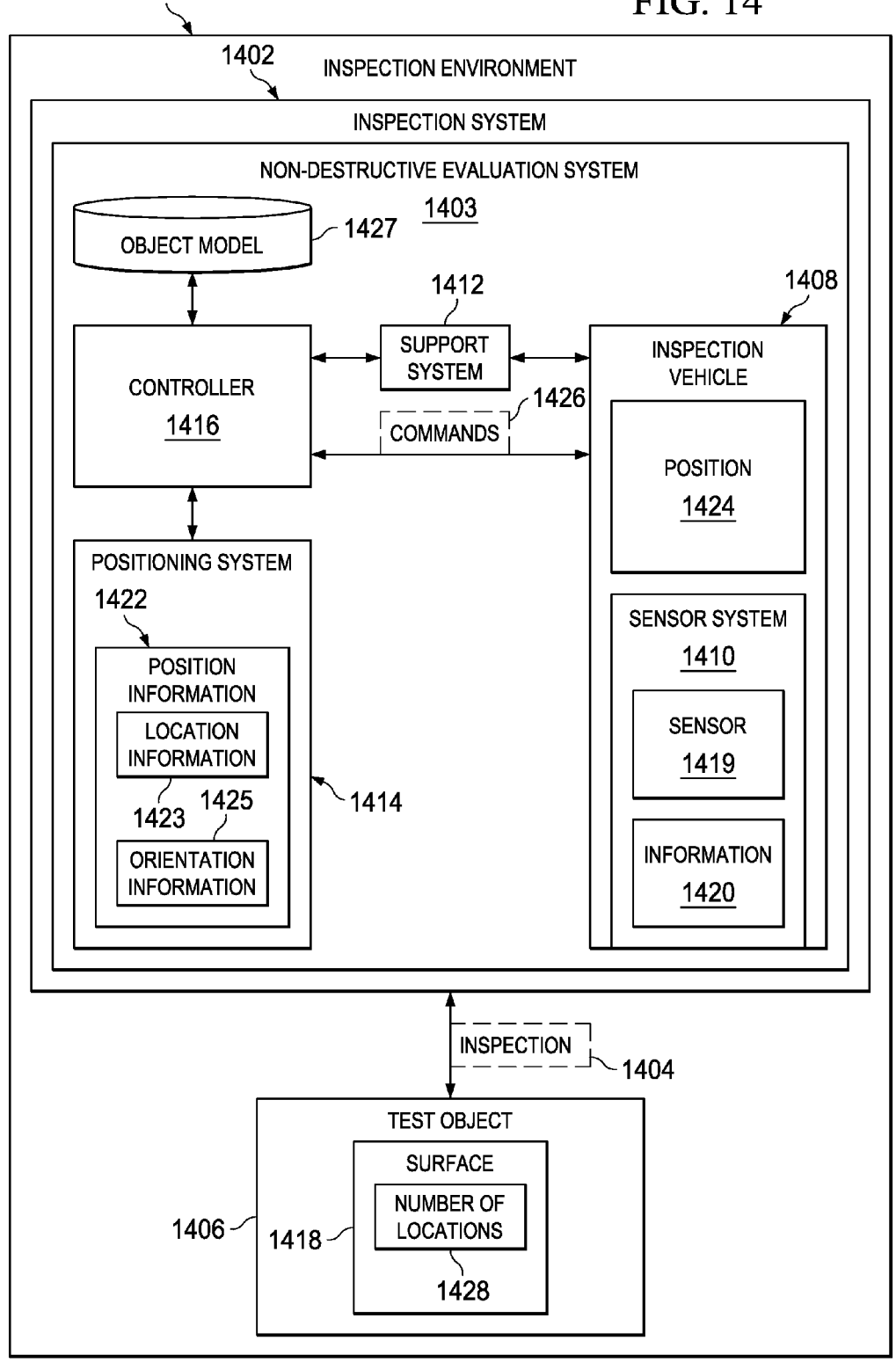
FIG. 14 is an illustration of an inspection environment in accordance with an illustrative embodiment.

With reference now to FIG. 14, an illustration of an inspection environment is depicted in accordance with an illustrative embodiment. Inspection environment 1400 is an example of an inspection environment that may be used to inspect test object 202 in FIG. 2.

Inspection system 1402 in inspection environment 1400 may be used to perform inspection 1404 of test object 1406. As depicted, inspection system 1402 is nondestructive evaluation system 1403.

In these illustrative examples, inspection system 1402 comprises inspection vehicle 1408, sensor system 1410, support system 1412, positioning system 1414, and controller 1416. Inspection vehicle 1408 is configured to move on surface 1418 of test object 1406. For example, inspection vehicle 1408 may have a size that is suitable for moving on surface 1418 of test object 1406 in a desirable manner.

As depicted, sensor system 1410 includes sensor 1419. Sensor 1419 may be implemented using sensor 208 in FIG. 2. In this illustrative example, sensor system 1410 is associated with inspection vehicle 1408 in these depicted examples.

Sensor system 1410 is configured to generate information 1420 about test object 1406. Information 1420 may be generated while inspection vehicle 1408 is on surface 1418 of test object 1406. Information 1420 may be used in determining whether an inconsistency is present in test object 1406.

In particular, sensor 208 from FIG. 2 may be used in inspection vehicle 1408 to perform inspection 1404 of test object 1406 in the form of ultrasound inspection. In particular, sensor 1419, when implemented using sensor 208, does not require a coupling medium. In the illustrative examples, sensor 208 allows for inspection 1404 to take the form of a laser ultrasound inspection of test object 1406.

Support system 1412 is connected to inspection vehicle 1408. Support system 1412 may include, for example, cables that connect inspection vehicle 1408 to a structure. In other words, support system 1412 may tether inspection vehicle 1408 to the structure.

Support system 1412 may include a number of different lines. For example, support system 1412 may include tether cables and/or tension cables to lift inspection vehicle 1408 and/or restrict movement of inspection vehicle 1408. Further, support system 1412 also may include lines that carry electrical power, data, light, and/or fluid for inspection vehicle 1408. In these illustrative examples, the lines may include optical fibers such as optical fibers for first array of optical fibers 306 and second array of optical fibers 308 for sensor 208 in FIG. 3.

In these illustrative examples, support system 1412 is configured to support inspection vehicle 1408 as inspection 1404 is being performed. For example, support system 1412 may support inspection vehicle 1408 in response to an undesired release of inspection vehicle 1408 from surface 1418 of test object 1406. This undesired release may be, for example, inspection vehicle 1408 slipping from surface 1418, falling off of surface 1418, sliding on surface 1418, and/or having some other type of undesired motion relative to surface 1418 of surface 1418.

Further, support system 1412 may limit the type of and/or range of motion of inspection vehicle 1408. In this manner, the possibility of undesired and/or unplanned movement of inspection vehicle 1408 may be reduced.

In these illustrative examples, positioning system 1414 may be used in determining a location of inspection vehicle 1408. In particular, positioning system 1414 may be used in determining position 1424 of inspection vehicle 1408 on test object 1406 with respect to a coordinate system for test object 1406. Position 1424 of inspection vehicle 1408 includes at least one of a location and an orientation of inspection vehicle 1408. The location may be defined using the coordinate system for test object 1406. The orientation may be defined using a number of angles for inspection vehicle 1408 relative to a number of axes for test object 1406.

For example, positioning system 1414 generates position information 1422. Position information 1422 may include location information 1423 and orientation information 1425. Location information 1423 may be used in determining the location of inspection vehicle 1408 relative to test object 1406. Orientation information 1425 may be used in determining the orientation of inspection vehicle 1408 relative to test object 1406.

In these illustrative examples, position information 1422 may take various forms. For example, position information 1422 may comprise a measured location and/or orientation for inspection vehicle 1408 relative to test object 1406. In other illustrative examples, position information 1422 may be information that may be used to calculate position 1424 of inspection vehicle 1408.

In these illustrative examples, positioning system 1414 may comprise a motion capture positioning system, an inertial navigation positioning system, and/or other suitable types of positioning systems. Of course, any type of positioning system configured to generate position information 1422 may be used in positioning system 1414.

Position information 1422 is sent to controller 1416. Position information 1422 may be sent continuously such that controller 1416 has access to the most current and up to date position information for inspection vehicle 1408. In some illustrative examples, position information 1422 may be sent to controller 1416 periodically and/or in response to some event.

Controller 1416 comprises hardware and may include software in these depicted examples. Controller 1416 may use position information 1422 and object model 1427 of test object 1406 to determine position 1424 of inspection vehicle 1408 with respect to the coordinate system for test object 1406. Object model 1427 may be a design for test object 1406, such as, for example, a three-dimensional computer-aided design (CAD) model. Further, object model 1427 includes coordinates for a coordinate system for test object 1406.

Further, controller 1416 may use position information 1422 to correlate information 1420 generated by sensor system 1410 with the coordinate system for test object 1406. As one illustrative example, images generated by sensor system 1410 may be registered with object model 1427 of test object 1406.

In this manner, information 1420 may be aligned with object model 1427 such that a location at which an inconsistency is identified may be more readily identifiable. Further, with these images being registered with object model 1427, evaluation of information 1420 generated over time may be performed more quickly and/or efficiently as compared to when the images are not registered with object model 1427.

Controller 1416 is configured to control the movement of inspection vehicle 1408 and the operation of sensor system 1410 for performing inspection 1404. For example, controller 1416 uses position information 1422 generated by positioning system 1414 to guide inspection vehicle 1408 towards and/or to maintain a desired location and/or desired orientation for inspection vehicle 1408 relative to test object 1406.

As one illustrative example, controller 1416 sends commands 1426 to cause inspection vehicle 1408 to move on surface 1418 of test object 1406 to perform inspection 1404 of test object 1406. In particular, inspection vehicle 1408 may move to number of locations 1428 to perform inspection 1404. Commands 1426 sent by controller 1416 may be based on position 1424 determined for inspection vehicle 1408.

With inspection system 1402, inspection vehicle 1408 may be selected as one that may be less complex and/or expensive than other inspection vehicles. For example, inspection vehicle 1408 may be selected as one that may be lower in cost and complexity.

For example, inspection vehicle 1408 does not need a computer system or other controller that includes artificial intelligence, neural-networks, or other types of programs. Instead, inspection vehicle 1408 may merely receive commands 1426 from controller 1416 to move to number of locations 1428 that have been selected for inspection 1404 at a rate and in a direction specified by controller 1416 in commands 1426. Also, with the use of controller 1416, controller 1416 may control other inspection vehicles in addition to inspection vehicle 1408 at the same time or at different times.

The different components in inspection system 1402 may allow for easier or quicker set ups of inspection system 1402 to perform inspections on different test objects. Further, inspection system 1402 also may allow for use of inspection vehicles that have a size and/or configuration that may make inspecting test object 1406 easier. This type of configuration may be useful with objects, such as aircraft that may have locations with areas that are difficult for human access.

With the use of positioning system 1414 and controller 1416, the planning of tests for inspection, and the guidance of inspection vehicle 1408 may be performed by controller 1416. In this manner, inspection vehicle 1408 does not need the intelligence or capability to perform its own planning for performing inspection 1404. This planning may include scheduling times at which testing is to be performed using sensor system 1410, planning movement to number of locations 1428, and/or other types of planning.

The illustration of inspection environment 1400 in FIG. 14 is not meant to imply physical or architectural limitations to the manner in which an illustrative embodiment may be implemented. Other components in addition to, and/or in place of, the ones illustrated may be used. Some components may be unnecessary. Also, the blocks are presented to illustrate some functional components. One or more of these blocks may be combined and/or divided into different blocks when implemented in an illustrative embodiment.

For example, inspection system 1402 may have one or more additional inspection vehicles in addition to inspection vehicle 1408. These additional inspection vehicles may be controlled by additional controllers, positioning systems, and/or support systems. In some illustrative examples, inspection by these additional inspection vehicles may be controlled using controller 1416 and positioning system 1414.

Figure 15:
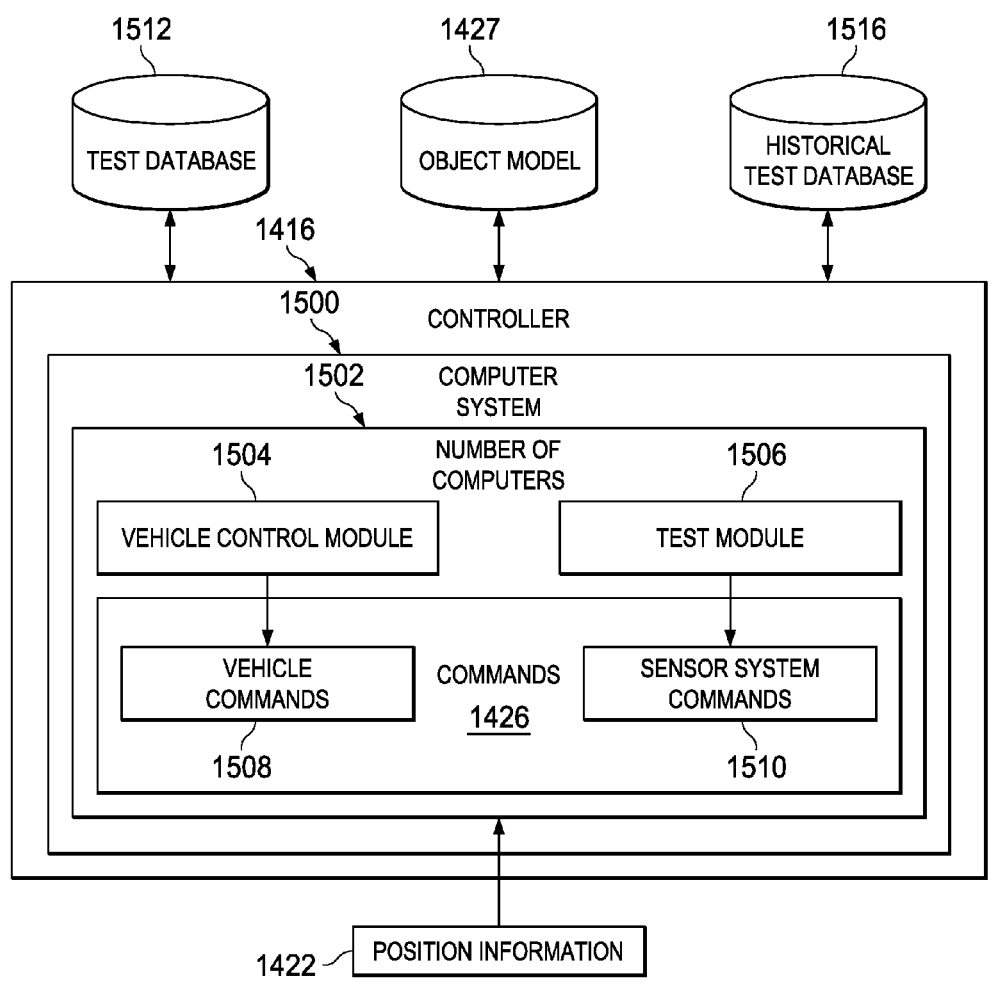
FIG. 15 is an illustration of a controller in accordance with an illustrative embodiment.

With reference now to FIG. 15, an illustration of a controller is depicted in accordance with an illustrative embodiment. In this illustrative example, components for controller 1416 are illustrated.

Controller 1416 comprises computer system 1500. In these illustrative examples, computer system 1500 may be comprised of number of computers 1502. When more than one computer is present in computer system 1500, these computers may be in communication with each other over a communications medium such as a network.

In these illustrative examples, controller 1416 includes vehicle control module 1504 and test module 1506 in computer system 1500. These modules may be implemented using hardware, software, or a combination of the two.

Vehicle control module 1504 is configured to generate vehicle commands 1508 and send vehicle commands 1508 to inspection vehicle 1408 in FIG. 14. Test module 1506 is configured to generate sensor system commands 1510 and send sensor system commands 1510 to inspection vehicle 1408.

In these illustrative examples, vehicle commands 1508 and sensor system commands 1510 are examples of the types of commands 1426 that may be generated by controller 1416. Vehicle commands 1508 are commands used to control the movement of inspection vehicle 1408. Sensor system commands 1510 are commands used to control the operation of sensor system 1410.

Vehicle commands 1508 and sensor system commands 1510 may take different forms depending on the particular implementation. For example, vehicle commands 1508 may be commands, such as turn five degrees, move five feet forward, stop, and other similar types of commands. Sensor system commands 1510 may include commands as to when to perform scans, what information to return, and other suitable types of commands.

In these illustrative examples, the generation of commands 1426 is performed using position information 1422 sent to controller 1416 by positioning system 1414. In generating commands 1426, test database 1512 is used by controller 1416 to identify a particular test to perform on test object 1406. In identifying a test, test database 1512 includes, for example, the types of tests to be performed, the locations where the tests are to be performed, when a test is to be performed, and other suitable types of information.

Object model 1427 is used to generate commands 1426 to move inspection vehicle 1408 to number of locations 1428 to perform inspection 1404 of test object 1406 in FIG. 14. Position information 1422 may be used to determine position 1424 of inspection vehicle 1408 with respect to the coordinate system for test object 1406 in object model 1427. With this correlation of coordinates, vehicle commands 1508 may be generated to move inspection vehicle 1408 to coordinates identified for number of locations 1428 in FIG. 14.

Additionally, position information 1422 also may be used by test module 1506 to generate sensor system commands 1510. These commands are generated to cause sensor system 1410 to generate information 1420 at number of locations 1428 based on knowing position 1424 of inspection vehicle 1408 relative to test object 1406 with respect to the coordinate system for test object 1406 in FIG. 3.

Further, position information 1422 may be used with information 1420 to register information 1420 using a common frame of reference for test object 1406. This common frame of reference may be, for example, a coordinate system for object model 1427. In this manner, coordinates for information 1420 may be aligned with coordinates for object model 1427. Registering information 1420 using the coordinate system for object model 1427 may allow analysis of information 1420, maintenance for test object 1406, identifying locations on test object 1406 having inconsistencies, and/or other operations to be performed more easily and efficiently as compared to performing these operations without registering information 1420.

In some cases, depending on the manner in which support system 1412 is implemented, vehicle control module 1504 also may generate commands 1426 to operate support system 1412. For example, if support system 1412 includes a motor, commands 1426 may be generated and sent to support system 1412 to operate the motor. Additionally, commands 1426 may include signals to activate a brake if a brake system is present in support system 1412.

Information 1420 may be received by test module 1506 in these illustrative examples. Information 1420 may be saved in historical test database 1516. Information 1420 may be associated number of locations 1428 for which information 1420 was generated. In these illustrative examples, test module 1506 may receive the current location and orientation of inspection vehicle 1408 through position information 1422 received from positioning system 1414.

In this manner, information about locations in which inconsistencies are present, but not considered to be undesired inconsistencies may be made. With the association of coordinates identifying where the information was generated for these inconsistencies with the information, planning of additional inspections to test these locations may be made. Further, a progression or non-progression of the inconsistencies also may be identified over time. This analysis may be used to determine whether other actions may be needed.

Figure 16:
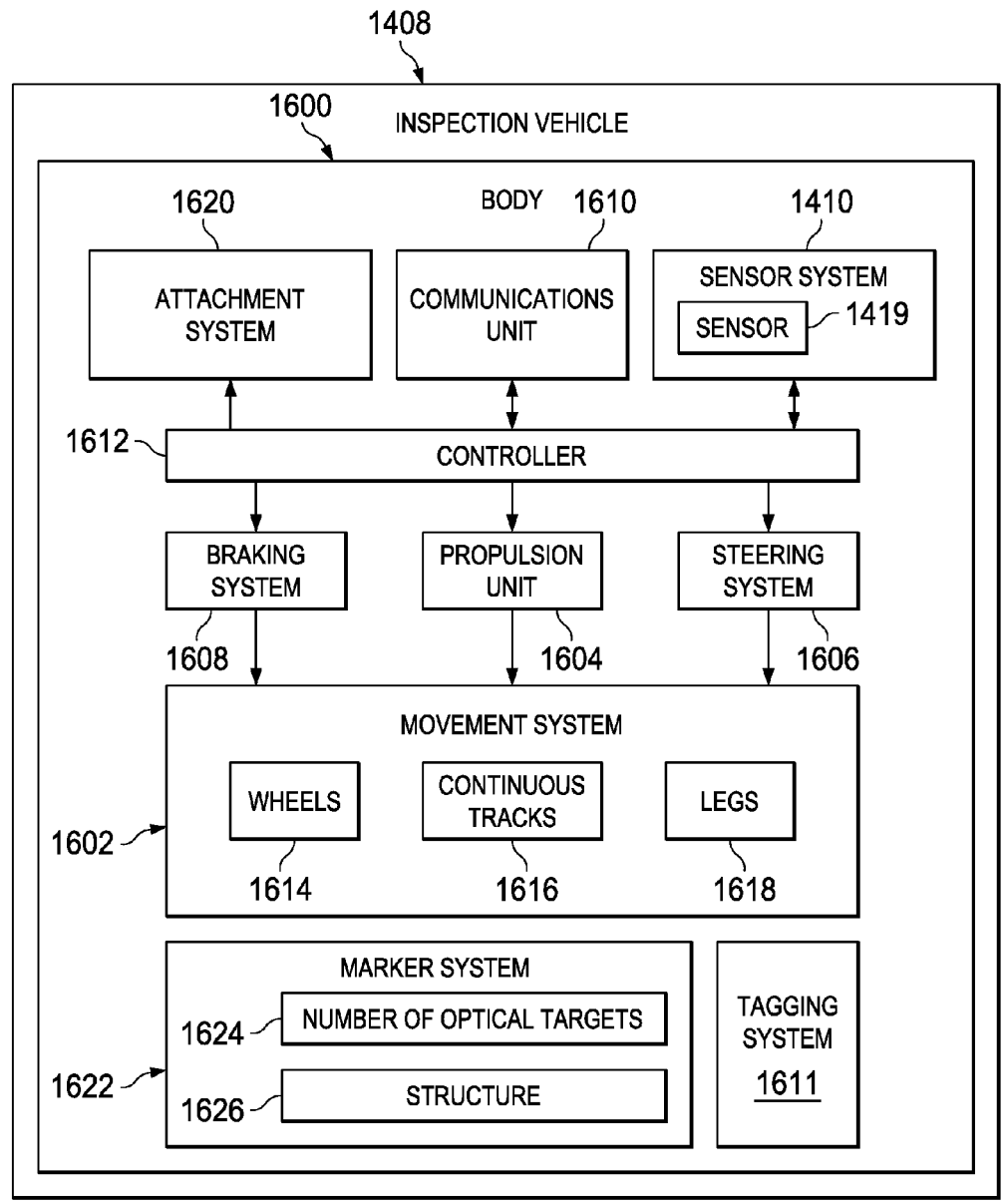
FIG. 16 is an illustration of components for an inspection vehicle in accordance with an illustrative embodiment.

With reference now to FIG. 16, an illustration of components for an inspection vehicle is depicted in accordance with an illustrative embodiment. In this depicted example, examples of components that may be present in inspection vehicle 1408 are depicted. The different components for inspection vehicle 1408 illustrated in FIG. 16 may be implemented using various components that are currently available for use in vehicles.

As illustrated, inspection vehicle 1408 includes body 1600, movement system 1602, propulsion unit 1604, steering system 1606, braking system 1608, communications unit 1610, sensor system 1410, and tagging system 1611.

Body 1600 provides a structure that other components in inspection vehicle 1408 may be connected to in these examples. Body 1600 may be, for example, without limitation, a frame, a uni-body, or some other suitable type of body.

Movement system 1602 comprises components configured to provide movement of inspection vehicle 1408. For example, movement system 1602 may comprise at least one of wheels 1614, continuous tracks 1616, legs 1618, and other suitable types of movement mechanisms.

Propulsion unit 1604 is configured to cause movement by movement system 1602. In other words, propulsion unit 1604 generates mechanical energy for movement system 1602. Propulsion unit 1604 may be, for example, an electrical motor.

Steering system 1606 is configured to control movement system 1602 in different directions. Braking system 1608 is used to slow and/or halt movement of movement system 1602. Steering system 1606 may change the direction in which movement system 1602 moves inspection vehicle 1408.

Communications unit 1610 is configured to allow for the reception of commands and the transmission of information. In these illustrative examples, communications unit 1610 may be a wireless communications unit. In other illustrative examples, communications may be provided through a physical connection. With a physical connection, communications unit 1610 may be, for example, a network interface card, a modem, or some other suitable type of communications unit.

Controller 1612 is configured to receive commands 1426 in FIG. 14. In response to these commands, controller 1612 controls the operations of movement system 1602, propulsion unit 1604, steering system 1606, and braking system 1608. In these illustrative examples, controller 1612 may be implemented using a processor, an application specific integration circuit, or some other type of circuit system.

In addition to these components, attachment system 1620 may be present in some illustrative examples. Attachment system 1620 may aide in attaching inspection vehicle 1408 to surface 1418 of test object 1406. In this manner, inspection vehicle 1408 may be able to move on inclined, vertical, and/or inverted surfaces without slipping. As a result, additional areas of test object 1406 may be reachable when using attachment system 1620 as compared to when attachment system 1620 is absent for inspection vehicle 1408.

In these illustrative examples, attachment system 1620 may take a number of different forms depending on the implementation. For example, attachment system 1620 may include at least one of a suction cup system, a pressure differential system, a magnetic system, and some other suitable type of system for attaching inspection vehicle 1408 to surface 1418 of test object 1406 in FIG. 14. A pressure differential system may be any system configured to generate a pressure differential on surface 1418 of test object 1406. A vacuum system is an example of one type of pressure differential system.

Also, depending on the type of system used in positioning system 1414, inspection vehicle 1408 also may include marker system 1622. Marker system 1622 is associated with body 1600. Marker system 1622 is configured to allow positioning system 1414 to determine position 1424 of inspection vehicle 1408. A single marker may be used to determine a location of inspection vehicle 1408. Multiple markers may be used to also determine an orientation of inspection vehicle 1408.

In these illustrative examples, marker system 1622 includes number of optical targets 1624. Number of optical targets 1624 may be associated with body 1600. In these illustrative examples, number of optical targets 1624 may take different forms. For example, an optical target in number of optical targets 1624 may be selected from one of a light-emitting diode, retro-reflective marker, paint, tape, and other suitable types of markers.

Number of optical targets 1624 is used by positioning system 1414 to determine a location of inspection vehicle 1408. Depending on the particular implementation, number of optical targets 1624 may be mounted on structure 1626 connected to inspection vehicle 1408. Marker system 1622 may be considered to be part of positioning system 1414 in some illustrative examples.

Sensor system 1410 is illustrated as being associated with inspection vehicle 1408 in this particular example. Sensor system 1410 may be integrated as part of inspection vehicle 1408, connected to inspection vehicle 1408, and/or removably connected to inspection vehicle 1408, depending on the particular implementation. In some cases, when sensor system 1410 is removably connected to body 1600 of inspection vehicle 1408, this system may be considered a separate component from inspection vehicle 1408.

Tagging system 1611 is configured to allow locations of interest on test object 1406 to be tagged. Locations of interest may include, for example, locations at which inconsistencies have been detected. Tagging a location may comprise forming some type of visual indication for the location. For example, tagging a location may include at least one of spraying paint at the location, applying ink to the location, applying a sticker to the location, marking the location with a chalk, and other suitable types of physical tagging operations.

Figure 17:
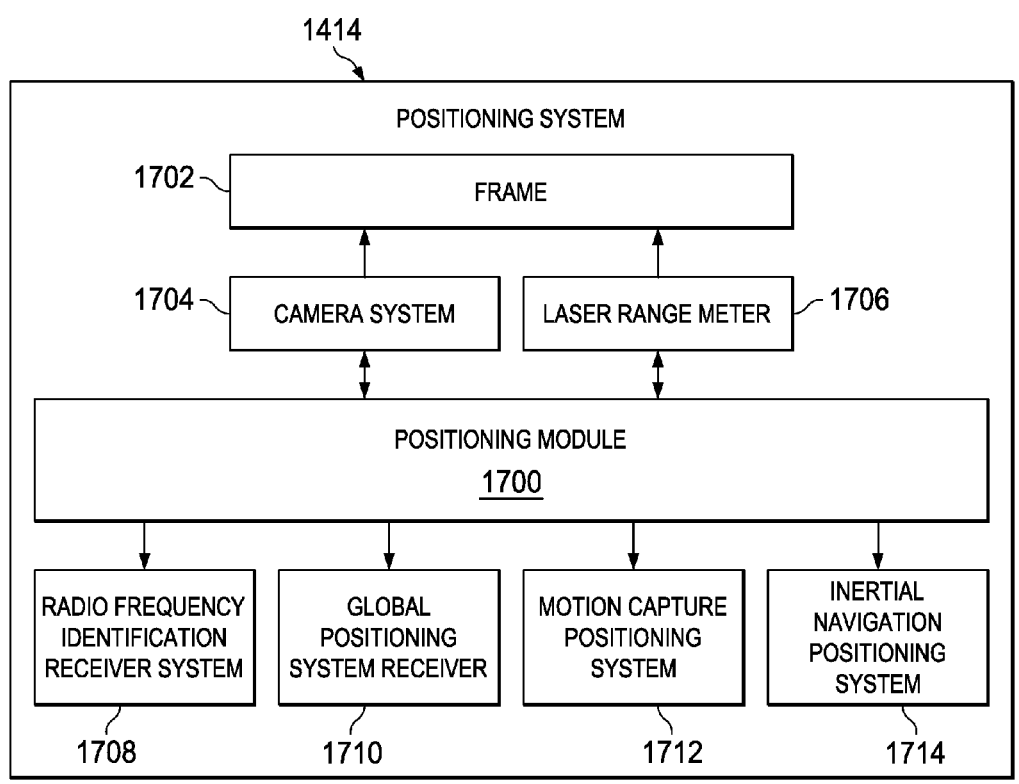
FIG. 17 is an illustration of a positioning system in accordance with an illustrative embodiment.

With reference now to FIG. 17, an illustration of a positioning system is depicted in accordance with an illustrative embodiment. In this illustrative example, components for positioning system 1414 are depicted.

Positioning system 1414 may include, for example, positioning module 1700, frame 1702, camera system 1704, and laser range meter 1706. Camera system 1704 and laser range meter 1706 may be implemented using currently available camera systems and laser range meter devices. Frame 1702 is a structure in which different components in positioning system 1414 may be mounted on or connected to in these examples. Frame 1702 may be, for example, without limitation, a stand, a ceiling mount, or some other suitable type of structure.

Camera system 1704 is configured to generate images. Camera system 1704 may be implemented using any camera configured to generate images. For example, camera system 1704 may include at least one of visible light cameras, infrared light cameras, and other suitable types of cameras.

Laser range meter 1706 is configured to measure distances to a target, such as inspection vehicle 1408. Laser range meter 1706 may have a laser and a unit configured to compute distances based on the laser light detected in response to a laser beam bouncing off of a target.

The images and distances along with a location and orientation of camera system 1704 and laser range meter 1706 may be used to generate position information 1422 by positioning module 1700. In other illustrative examples, this information may be position information 1422 and sent back to controller 1416, which then determines position 1424 of inspection vehicle 1408.

Positioning module 1700 also may change the orientation of camera system 1704, laser range meter 1706, or both. The change in orientation of these components may be performed to track inspection vehicle 1408 as inspection vehicle 1408 moves on test object 1406 in FIG. 14. The change in orientation of camera system 1704, laser range meter 1706, or both may be controlled by controller 1416, positioning module 1700, or a combination of the two. For example, controller 1416 may identify targets to be tracked from images generated by camera system 1704.

In other illustrative examples, positioning system 1414 may take other forms. For example, positioning system 1414 may include radio frequency identification receiver system 1708, global positioning system receiver 1710, and/or other types of positioning systems in addition to, and/or in place of, camera system 1704 and laser range meter 1706. In some illustrative examples, positioning system 1414 may include motion capture positioning system 1712 and/or inertial navigation positioning system 1714.

With radio frequency identification receiver system 1708, radio frequency identification receiver systems may be positioned on frame 1702. Radio frequency identification tags may be associated with inspection vehicle 1408. Based on the strength and direction at which signals are received from these tags, positioning module 1700 may determine a location and orientation of inspection vehicle 1408.

With global positioning system receiver 1710, some components of positioning system 1414 may actually be located on inspection vehicle 1408 rather than as a separate component. Global positioning system receiver 1710 may generate coordinate information about a location of inspection vehicle 1408. This coordinate information may be in latitude, longitude, and elevation.

This coordinate information may be translated into a coordinate system for test object 1406 in these illustrative examples. This translation may be performed by positioning module 1700 and/or from one coordinate system to another coordinate system by controller 1416.

With motion capture positioning system 1712, the positions of retro-reflective markers are tracked using two or more integrated illuminators. When three or more retro-reflective markers are grouped in a known configuration and placed on inspection vehicle 1408, the positions of the three or more markers and their known relative offset positions can be used to determine the location and orientation of inspection vehicle 1408.

As inspection vehicle 1408 is moved within the field-of-view of the two or more cameras, marker positions are continuously tracked and used to generate substantially real-time location and orientation measurements of inspection vehicle

1408. Using this process, inspection vehicle 1408 can be tracked while moving on surface 1418 of test object 1406 during inspection 1404 in FIG. 14.

In addition, if three or more makers are placed on surface 1418 of test object 1406, the location and orientation of inspection vehicle 1408 relative to surface 1418 may be obtained. Using motion capture positioning system 1712, multiple inspection vehicles may be tracked simultaneously. Motion capture positioning system 1712 may be controlled using positioning module 1700.

Inertial navigation system 1714 is configured to process acceleration and rotational rate data from an inertial measurement unit (IMU) sensor. This processing may be performed to determine a location and orientation of inspection vehicle 1408 relative to a starting location.

The illustration of radio frequency identification receiver system 1708, global positioning system receiver 1710, and motion capture positioning system 1712 are only examples of positioning systems. For example, other types of positioning systems may be used in addition to, and/or in place of, camera system 1704 and laser range meter 1706.

In these illustrative examples, other types of systems also may be used in place of, and/or in addition to, these systems depending on the particular implementation. For example, positioning system 1414 may include systems, such as a camera tracking system, a laser tracking system, and/or some other suitable type of positioning system. Additionally, these systems may be implemented using currently available systems to determine the position and orientation of objects.

Figure 18:
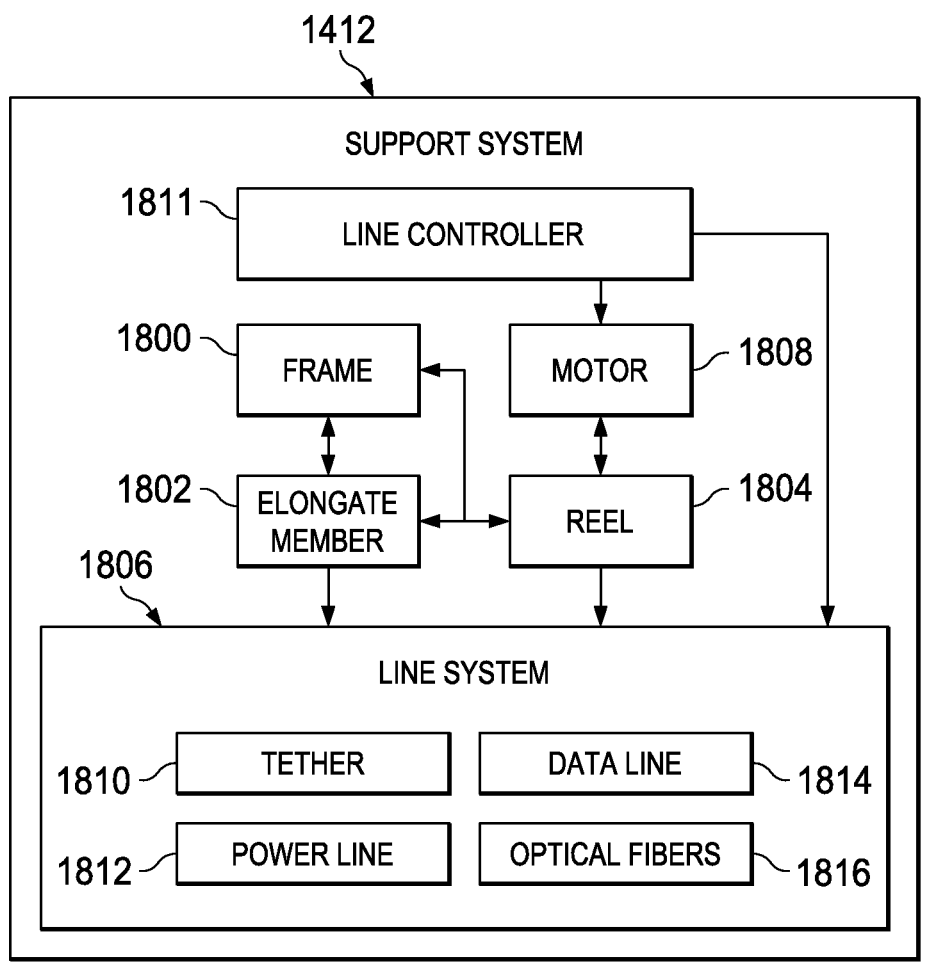
FIG. 18 is an illustration of a support system in accordance with an illustrative embodiment.

With reference now to FIG. 18, an illustration of a support system is depicted in accordance with an illustrative embodiment. In this illustrative example, support system 1412 includes frame 1800.

Elongate member 1802 may be attached to frame 1800. Additionally, reel 1804 may be connected to elongate member 1802 and/or frame 1800. Line system 1806 may be connected to reel 1804 and elongate member 1802. Line system 1806 connects support system 1412 to inspection vehicle 1408.

Elongate member 1802 may take various forms. For example, elongate member 1802 may be a rod, a boom, or some other suitable type of elongate member. In some cases, elongate member 1802 also may be flexible.

In these illustrative examples, line system 1806 is one or more lines. Line system 1806 may restrict or aide in managing movement of inspection vehicle 1408.

For example, reel 1804 may be a tensionable reel and may include a brake unit. Reel 1804 may be configured to hold a line in line system 1806 and supply a level of tension to the line. Further, reel 1804 may reduce the slack in line system 1806. A tensionable reel is a reel in which the reel is biased to rotate in a direction to take up slack that may occur in line system 1806. The brake unit may halt and/or reduce the rate at which the line being held by reel 1804 is allowed to be drawn out from the reel.

As a result, support system 1412 may reduce the possibility of an undesired release of inspection vehicle 1408 from surface 1418 of test object 1406 causing undesired effects to inspection vehicle 1408, test object 1406, and/or other objects and/or personnel in inspection environment 1400. An undesired release of inspection vehicle 1408 from surface 1418 may be, for example, a slippage, falling, or sliding of inspection vehicle 1408 when inspection vehicle 1408 is on surface 1418 of test object 1406. In this manner, support system 1412 may provide the equivalent of a safety net for inspection vehicle 1408.

Motor 1808 may be used to turn reel 1804 if reel 1804 is not a tensionable reel. In particular, motor 1808 may turn reel 1804 in a manner that increases tension or reduces slack in line system 1806. Reel 1804 may increase tension in line system 1806 in a manner that may reduce or halt movement of inspection vehicle 1408. Further, reel 1804 also may be used in lifting and/or moving inspection vehicle 1408 in some illustrative examples.

Additionally, in these illustrative examples, support system 1412 may include line controller 1811. Line controller 1811 is configured to control a set of lines in line system 1806 connected to line controller 1811 to perform at least one of supporting inspection vehicle 1408 in response to an undesired release of inspection vehicle 1408 from surface 1418 of test object 1406, slowing the movement of inspection vehicle 1408, halting the movement of inspection vehicle 1408, supporting inspection vehicle 1408 as inspection vehicle 1408 moves on surface 1418 of test object 1406, lifting inspection vehicle 1408, and other suitable operations.

Further, line controller 1811 also may be configured to control a set of lines in line system 1806 in response to a number of commands received from controller 1416. Line controller 1811 also may control motor 1808 and/or reel 1804 to control line system 1806. Of course, in other illustrative examples, line controller 1811 may not be present in support system 1412.

In these illustrative examples, line system 1806 includes tether 1810, power line 1812, data line 1814, and optical fibers 1816. Of course, line system 1806 may include other types of lines depending on the implementation. Tether 1810 provides support for controlling movement of inspection vehicle 1408. Power line 1812 may provide power to inspection vehicle 1408. Data line 1814 may provide a communications link to inspection vehicle 1408.

As depicted, optical fibers 1816 may carry optical signals. In these illustrative examples, optical fibers 1816 may include optical fibers for first array of optical fibers 306 and second array of optical fibers 308 in FIG. 3.

For example, first array of optical fibers 306 in optical fibers 1816 may carry optical signals configured to be transmitted by sensor 1419 to surface 1418 of test object 1406 in a manner that causes sound waves to travel within test object 1406. These sound waves may result in response sound waves in test object 1406 caused by the sound waves generated by the optical signals. These sound waves may be detected using optical signals transmitted and detected by second array of optical fibers 308 in optical fibers 1816.

The illustration of different components in inspection environment 1400 in FIGS. 15-18 are presented as some examples in which these components may be implemented. The illustration of these components is not meant to imply physical or architectural limitations to the manner in which an illustrative embodiment may be implemented. Other components may be used in addition to, and/or in place of, the ones illustrated. Further, the blocks illustrated in these figures may be combined or divided into different blocks depending on the particular implementation.

Figure 19:
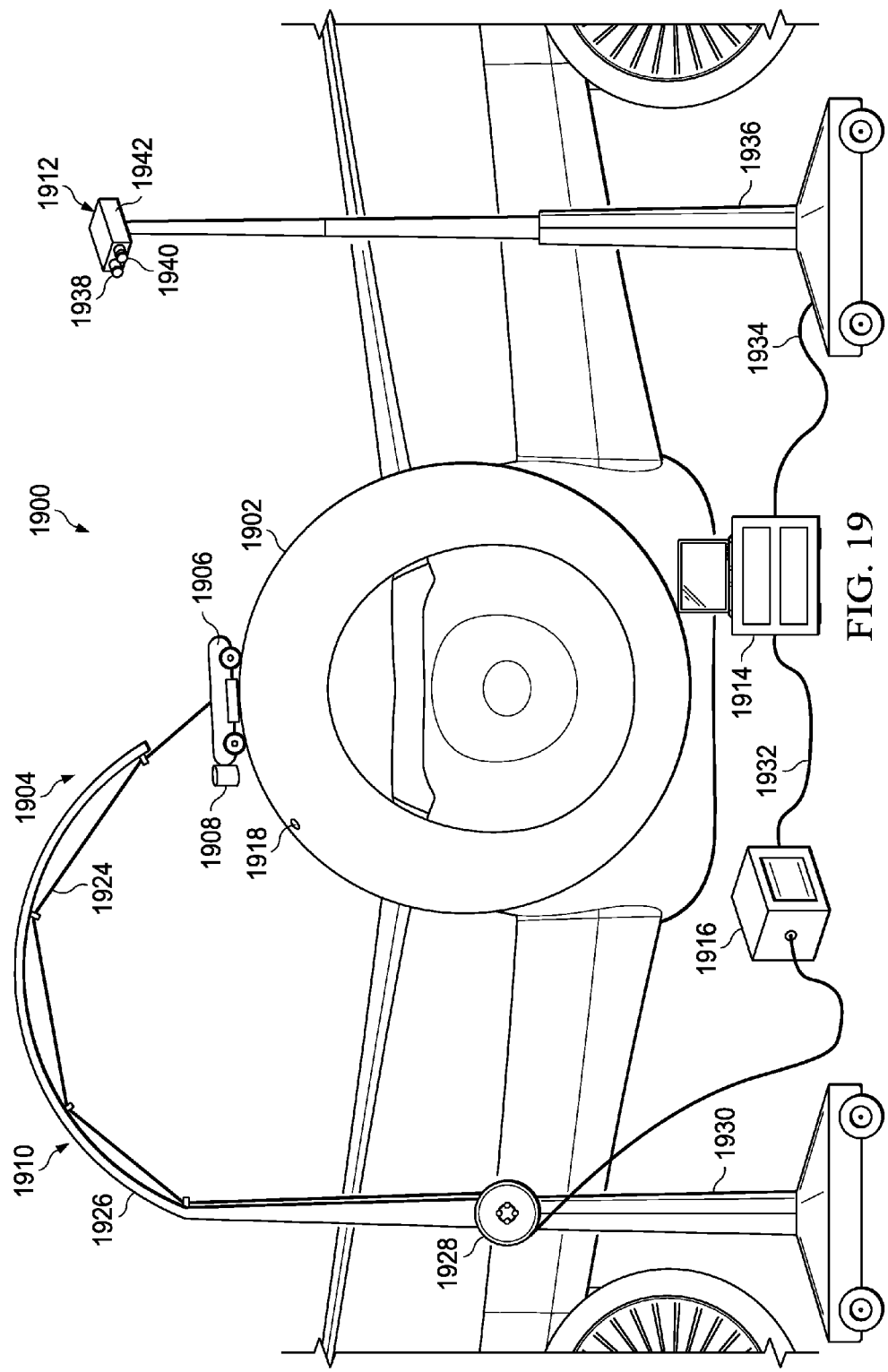
FIG. 19 is an illustration of a physical implementation of an inspection environment in accordance with an illustrative embodiment.

With reference now to FIG. 19, an illustration of a physical implementation of an inspection environment is depicted in accordance with an illustrative embodiment. Inspection environment 1900 is an example of one implementation for inspection environment 1400 shown in block form in FIG. 14. In this depicted example, inspections may be performed on a test object in the form of aircraft 1902 in inspection environment 1900 using inspection system 1904.

As illustrated, inspection system 1904 includes inspection vehicle 1906, sensor system 1908, support system 1910, positioning system 1912, controller 1914, and coherent light source and interferometer system 1916. Of course, inspection system 1904 may include other components not shown or described in this particular example.

As depicted, inspection vehicle 1906 moves on surface 1918 of aircraft 1902. Inspection vehicle 1906 is an example of a physical implementation for inspection vehicle 1408 shown in block form in FIG. 14 and FIG. 16. Inspection vehicle 1906 may move to different locations on surface 1918 of aircraft 1902 to perform inspections of aircraft 1902.

Sensor system 1908 is associated with inspection vehicle 1906 in a manner that allows sensor system 1908 to inspect aircraft 1902. In these illustrative examples, sensor system 1908 is an example of an implementation for sensor system 1410 shown in block form in FIG. 14 and FIG. 16. In particular, sensor 1419 in FIG. 14 may take the form of sensor 208 as illustrated in block form in FIG. 3. With sensor system 1908, ultrasonic inspection may be performed on aircraft 1902.

In this illustrative example, line system 1924 in support system 1910 is connected to inspection vehicle 1906. Line system 1924 is also connected to rod 1926 in reel 1928 in support system 1910. Line system 1924 includes a tether, optical fibers, and other suitable types of lines. Other lines may be included in line system 1924. These lines may be at least one of a power line, a data line, and other suitable lines.

Rod 1926 is a flexible rod in this illustrative example and is connected to frame 1930 in support system 1910. In this illustrative example, coherent light source and interferometer system 1916 is connected to optical fibers within line system 1924. These optical fibers extend to sensor system 1908 in these illustrative examples.

Coherent light source and interferometer system 1916 is configured to generate coherent light for use in sensor system 1908. In particular, the coherent light may be used to generate sound signals within aircraft 1902. Further, coherent light source and interferometer system 1916 is also configured to analyze movement in surface 1918 that occurs in response to the coherent light generating sound signals within aircraft 1902.

Reel 1928 is mounted on frame 1930. Reel 1928 is a tensionable reel in these illustrative examples. Reel 1928 may be operated to change the tension in line system 1924. In these illustrative examples, reel 1928 may be controlled by controller 1914 to selectively manage movement of inspection vehicle 1906. As a result, line system 1924 may be reeled in or let out depending on the desired movement for inspection vehicle 1906.

Controller 1914 is connected to various components in inspection system 1904 through cables. For example, cable 1932 provides a connection from controller 1914 to coherent light source and interferometer system 1916 and to line system 1924 at reel 1928. Cable 1934 provides a connection from controller 1914 to positioning system 1912. These cables may include at least one of electrical and optical lines that may be used to carry information such as data and commands.

Positioning system 1912 is comprised of frame 1936, laser range meter 1938 and camera 1940. Laser range meter 1938 and camera 1940 are located within housing 1942 of positioning system 1912. Laser range meter 1938 may be used to generate information to identify the location and orientation of inspection vehicle 1906.

Information generated by positioning system 1912 is sent to controller 1914. Controller 1914 then generates commands for inspection vehicle 1906. Additionally, commands or signals also may be sent to operate sensor system 1908 in these illustrative examples.

Figure 20:
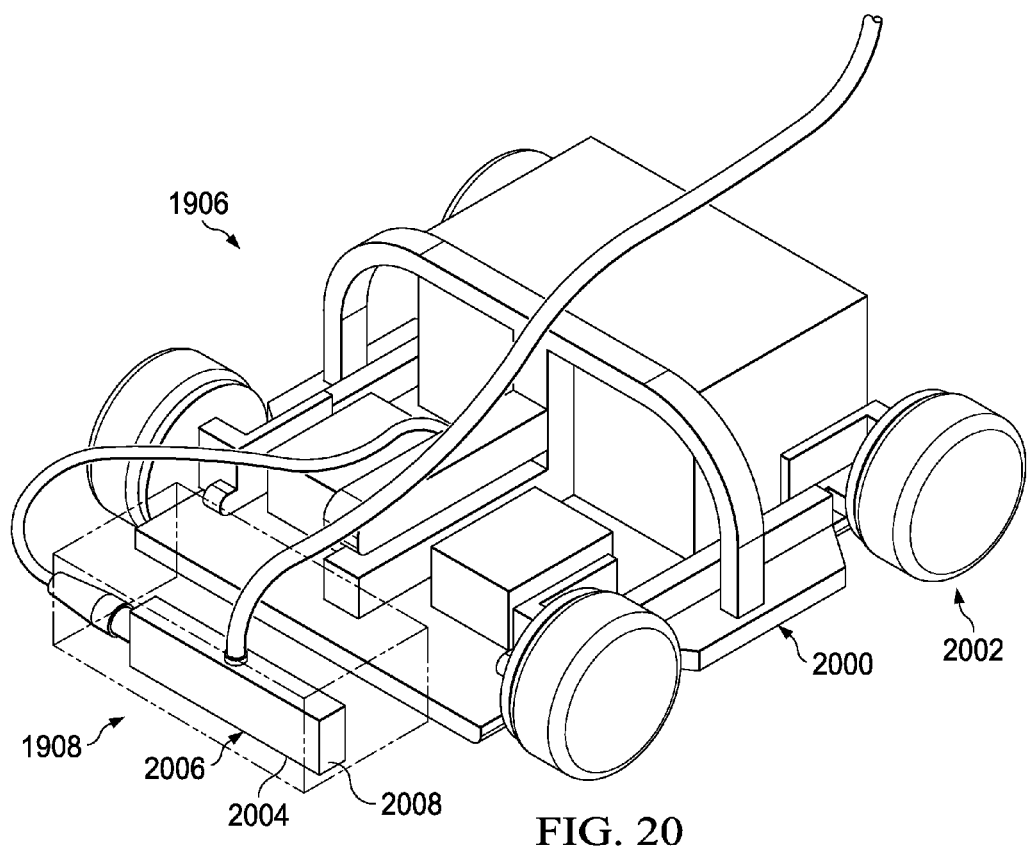
FIG. 20 is an illustration of an inspection vehicle in accordance with an illustrative embodiment.

With reference now to FIG. 20, an illustration of an inspection vehicle is depicted in accordance with an illustrative embodiment. In this example, an isometric view of inspection vehicle 1906 is shown.

Inspection vehicle 1906 has body 2000. Body 2000 is an example of one physical implementation for body 1600 for inspection vehicle 1408 shown in block form in FIG. 16. Wheels 2002 are attached to body 2000. Wheels 2002 are examples of wheels 1614 in movement system 1602 in inspection vehicle 1408 in FIG. 16.

In this illustrative example, sensor system 1908 includes sensor 2004. Sensor structure 2006 for sensor 2004 takes the form of housing 2008. Sensor structure 2006 with housing 2008 is an example of one implementation for sensor structure 300 in sensor 208 in FIG. 3.

In this illustrative example, housing 2008 may contain an ultrasound source and an ultrasound detector, such as a first array of optical fibers and a second array of optical fibers. For example, ultrasound source 500 and ultrasound detector 700 in sensor structure 902 as depicted in FIG. 9 are examples of components that may be used to implement sensor system 1908. For example, sensor structure 2006 may be implemented using sensor structure 902 and may contain ultrasound source 500 and ultrasound detector 700 in the manner illustrated in FIG. 9.

Figure 21:
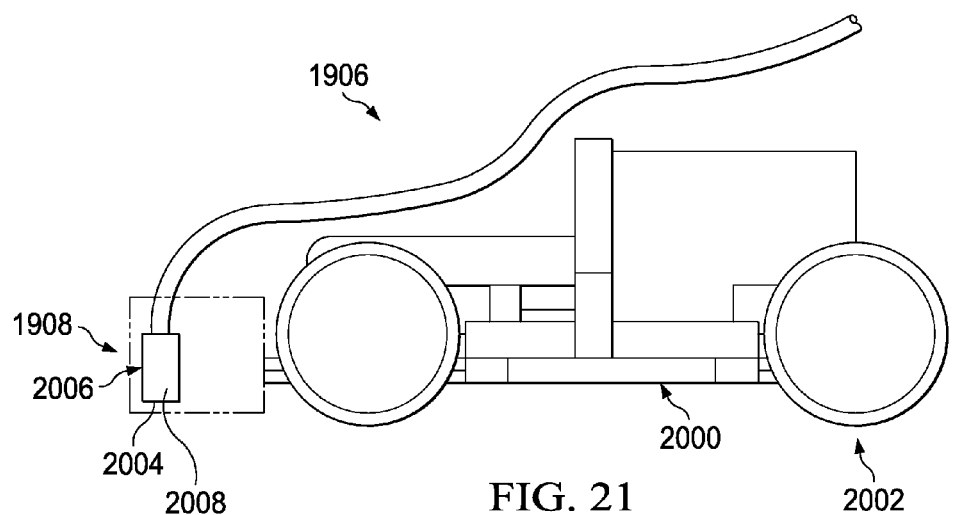
FIG. 21 is an illustration of a side view of an inspection vehicle in accordance with an illustrative embodiment.

In FIG. 21, an illustration of a side view of inspection vehicle 1906 is depicted in accordance with an illustrative embodiment.

Figure 22:
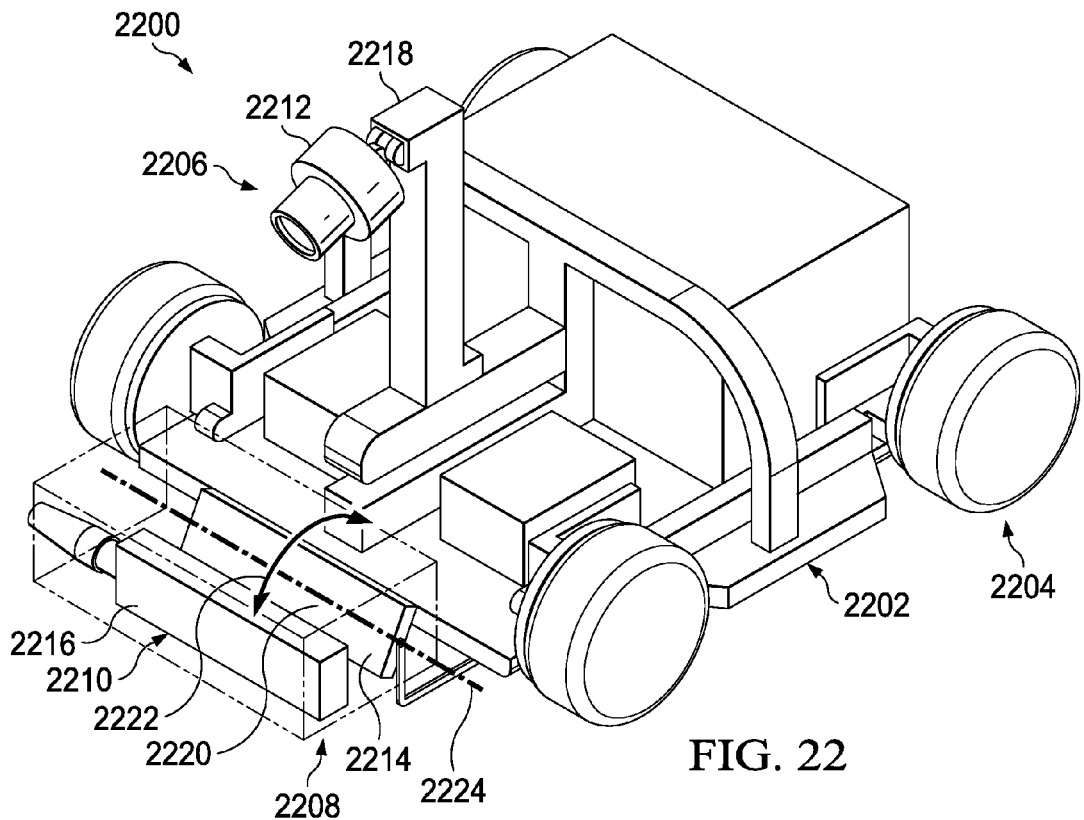
FIG. 22 is an illustration of another example of an inspection vehicle in accordance with an illustrative embodiment.

Turning now to FIG. 22, an illustration of another example of an inspection vehicle is depicted in accordance with an illustrative embodiment. In this depicted example, inspection vehicle 2200 is an example of another inspection vehicle that may be used in place of inspection vehicle 1906 within inspection system 1904 as illustrated in FIGS. 19-21

Inspection vehicle 2200 includes body 2202, wheels 2204, attachment system 2206, and sensor system 2208. As depicted, body 2202 provides a structure for other components in inspection vehicle 2200. Body 2202 is an example of one implementation of body 1600 for inspection vehicle 1408 in FIG. 16.

Wheels 2204 are examples of wheels 1614 in movement system 1602 in inspection vehicle 1408 in FIG. 16. Attachment system 2206 is a structure that may be attached to line system 1924 in FIG. 19. In this illustrative example, sensor system 2208 includes sensors 2210 and camera 2212. In this illustrative example, sensor 2210 is an example of an implementation for sensor 208 as illustrated in block form in FIG. 2 and FIG. 3.

As depicted, sensor 2210 includes first housing 2214 and second housing 2216. First housing 2214 and second housing 2216 are examples of an implementation for sensor structure 300 in sensor 208 in as depicted in block form in FIG. 3.

In this illustrative example, a first array of optical fibers for an ultrasound source is located in first housing 2214. A second array of optical fibers for an ultrasound detector is located in second housing 2216 in this illustrative example.

Camera 2212 may be part of a positioning system for guiding inspection vehicle 2200. Additionally, camera 2212 also may be used for providing alignment between the first array of optical fibers in first housing 2214 and the second array of optical fibers in second housing 2216. This alignment may be provided through the positioning of first housing 2214.

As depicted, first housing 2214 is moveably mounted on frame 2218 on body 2202 of inspection vehicle 2200. Camera 2212 may generate images that may be used to determine whether the first light emitted from the first array of optical fibers for the ultrasound source in first housing 2214 are aligned with the second light emitted by the second array of optical fibers for the ultrasound detector in second housing 2216.

Further, camera 2212 also may be used to perform visual inspection of a test object. The movement of first housing 2214 may be performed using actuator 2220 in this illustrative example. As depicted, actuator 2220 is connected to first housing 2214 and may operate to move first housing 2214 in the direction of arrow 2222 about axis 2224.

Figure 23:
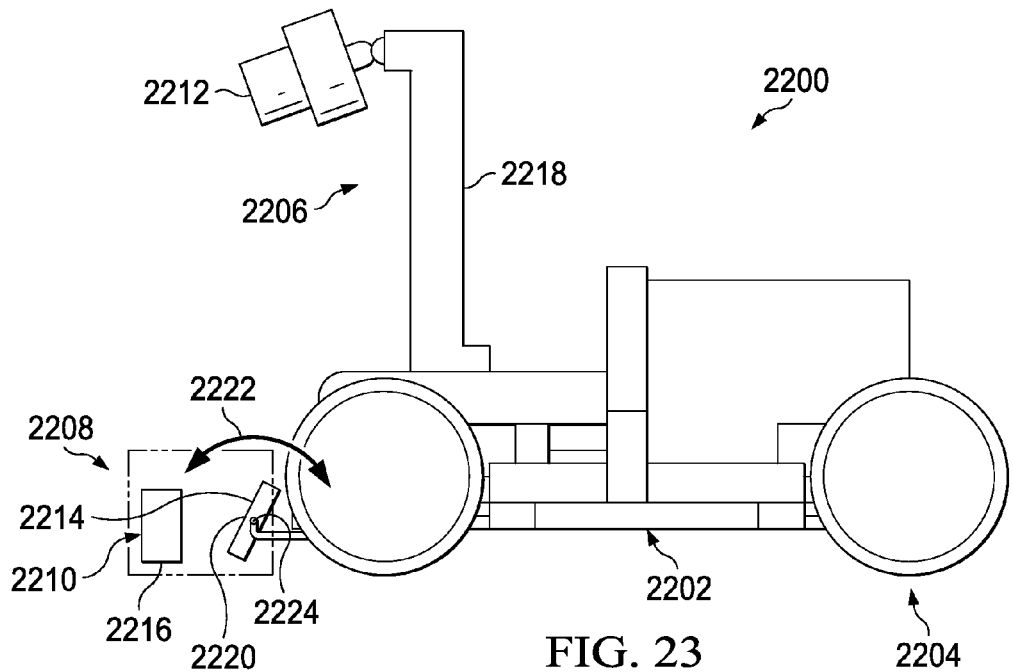
FIG. 23 is an illustration of a side view of an inspection vehicle in accordance with an illustrative embodiment.

FIG. 23 is an illustration of a side view of inspection vehicle 2200 in FIG. 22.

The illustration of inspection environment 1900 in FIG. 19, inspection vehicle 1906 in FIGS. 19-21, and inspection vehicle 2200 in FIGS. 22-23 are only examples of some implementations for an inspection vehicle and inspection vehicles. These illustrative examples are not meant to limit the manner in which other illustrative embodiments may be implemented.

For example, inspection system 1904 may include additional inspection vehicles in addition to inspection vehicle 1906 to inspect aircraft 1902. Further, other types of support systems other than rod 1926 with reel 1928 on frame 1930 may be used in support system 1910. Other support systems may include, for example, without limitation, a robotic arm, a crane, or some other suitable type of support system.

In still other illustrative examples, the sensor system on an inspection vehicle may include other sensors in addition to the ultrasound inspection system using coherent light as depicted in these examples. For example, sensor system 1908 on inspection vehicle 1906 and sensor system 2208 on inspection vehicle 2200 may be other types of sensor systems, such as a piezoelectric ultrasonic sensor system, an eddy current sensor system, a magnetic and optical imaging system, a thermography system, a laser shearography system, and other suitable types of non-destructive evaluation systems.

In still other illustrative examples, an inspection vehicle may have other types of movement systems other than those that use wheels. For example, an inspection vehicle may have tracks. Further, an inspection vehicle also may include a suction cup or vacuum system to maintain a position on the surface of aircraft 1902. A suction cup or vacuum system may provide additional support for an inspection vehicle when non-planar surfaces, angled surfaces, and other surfaces are present.

The different components shown in FIGS. 19-23 may be combined with components in FIGS. 14-18 used with components in FIGS. 14-18, or a combination of the two. Additionally, some of the components in FIGS. 19-23 may be illustrative examples of how components shown in block form in FIGS. 14-18 can be implemented as physical structures.

Figure 24:
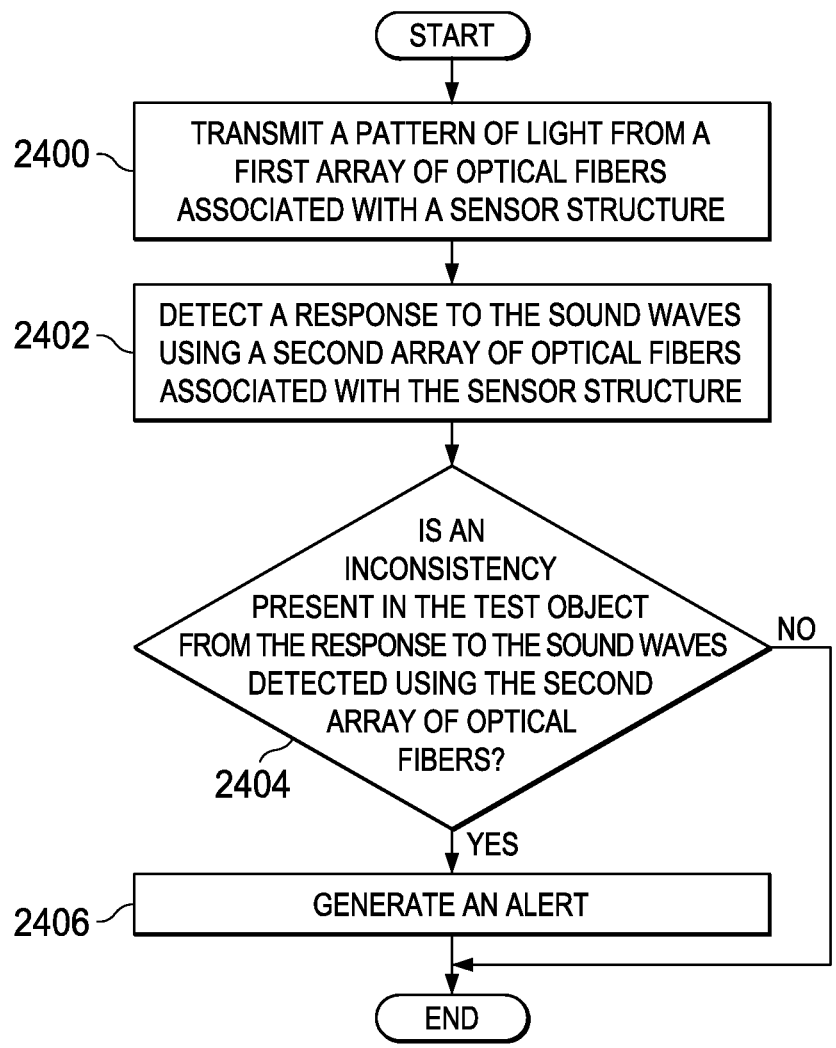
FIG. 24 is an illustration of a flowchart of a process for inspecting a test object in accordance with an illustrative embodiment.

Turning now to FIG. 24, an illustration of a flowchart of a process for inspecting a test object is depicted in accordance with an illustrative embodiment. The process illustrated in FIG. 24 may be implemented in an ultrasound inspection system such as ultrasound inspection system 204 in FIG. 2.

The process begins by transmitting a pattern of light from a first array of optical fibers associated with a sensor structure (operation 2400). The pattern of light is configured to cause sound waves in the test object when the pattern of light encounters the test object.

The process detects a response to the sound waves using a second array of optical fibers associated with the sensor structure (operation 2402). The second array of optical fibers transmits a second pattern of light in a manner that generates a response. This response is comprised of light that may have changes from the light in the response. The changes may be a result of changes in the surface caused by the response to the sound waves.

A determination is made as to whether an inconsistency is present in the test object from the response to the sound waves detected using the second array of optical fibers (operation 2404).

If an inconsistency is detected as being present in the test object, an alert is generated (operation 2406) with the process terminating thereafter. When an alert is generated, the test object may then be reworked or discarded. In some illustrative examples, operation 2406 may generate additional types of output in addition to the alert. For example, an image, a report, or both also may be generated in addition to the alert.

With reference again to operation 2404, if an inconsistency is not detected in the test object, the process also terminates. In this case, the test object has passed the inspection.

Figure 25:
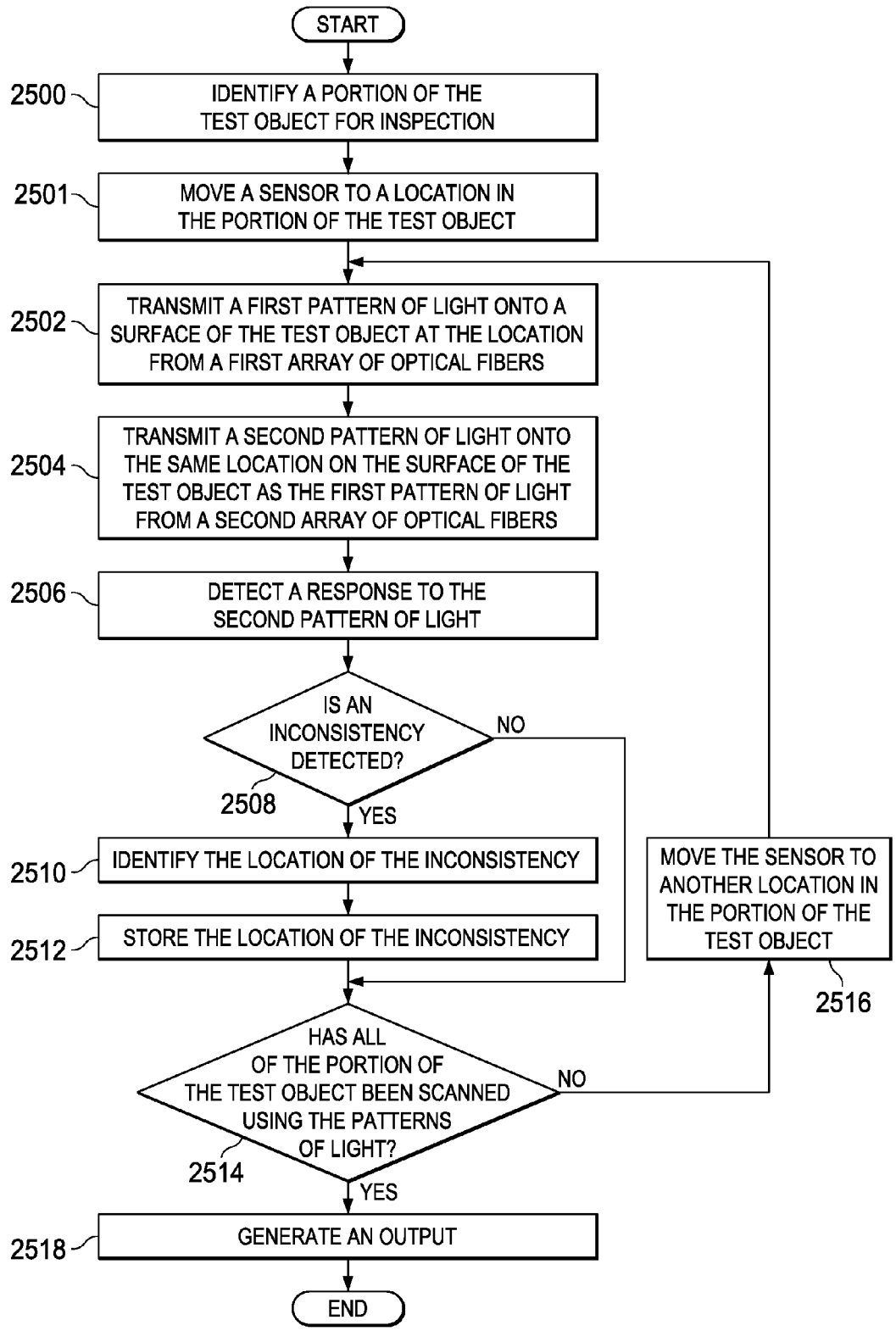
FIG. 25 is an illustration of a flowchart of a process for scanning a test object in accordance with an illustrative embodiment.

Turning now to FIG. 25, an illustration of a flowchart of a process for scanning a test object is depicted in accordance with an illustrative embodiment. In this illustrative example, the process in FIG. 25 may be implemented using ultrasound inspection system 204 in FIG. 2.

The process begins by identifying a portion of the test object for inspection (operation 2500). This portion of the test object may be some or the entire surface of the test object. For example, the portion of the test object may be a side, an edge, a radius, or some other portion of the test object.

A sensor is then moved to a location in the portion of the test object (operation 2501). In operation 2501, an orientation of the sensor may be adjusted to take into account a non-planar feature on the test object.

For example, the sensor may be positioned such that the pattern of light encompasses a non-planar feature not easily scanned by currently available laser ultrasound inspection systems. The non-planar feature may be, for example, a radius. The sensor may be moved in a linear direction along the length the radius.

In another illustrative example, the sensor may be positioned such that the pattern of light encompasses the margin of a part close to an edge where ultrasound coupling is difficult to achieve using currently available laser ultrasound inspection systems.

The process transmits a first pattern of light onto a surface of the test object at the location from a first array of optical fibers (operation 2502). In this illustrative example, the ray of light is transmitted in pulses and in a manner configured to cause sound waves in the test object. The location is a location in the portion of the test object that is to be inspected.

The process transmits a second pattern of light onto the same location on the surface of the test object as the first pattern of light from a second array of optical fibers (operation 2504). A response to the second pattern of light is detected (operation 2506). The response to the second pattern of light may be analyzed to identify a response to the sound waves that reach the surface of the test object.

A determination is made as to whether an inconsistency is detected (operation 2508). If an inconsistency is detected, the location of the inconsistency is identified (operation 2510). This location may be identified based on the response to sound waves detected using the response to the second pattern of light. The location of the inconsistency is stored (operation 2512).

A determination is made as to whether all of the portion of the test object has been scanned using the patterns of light (operation 2514). If all of the test object has not been scanned, the process moves the sensor to another location in the portion of the test object (operation 2516), with the process then returning to operation 2502 as described above.

If all of the portion of the test object has been scanned in operation 2514, an output is generated (operation 2518) with the process terminating thereafter. In operation 2518, the output may depend on whether one or more inconsistencies have been identified in the test object. If an inconsistency has been identified, at least one of an alert, an image with one or more graphical images identifying inconsistencies, a report, and other suitable types of output may be generated. Turning back to operation 2508, if an inconsistency is not detected, the process proceeds to operation 2514 as described above.

The different operations performed in FIG. 24 and FIG. 25 may be applied to test objects with planar and non-planar surfaces. These different operations may be performed for test objects that have non-planar features such as a radius, an edge, a groove, a ramp, a ply drop, a filler noodle, and other non-planar features.

Additionally, the different operations in FIG. 24 and FIG. 25 may be performed to inspect test objects more quickly than currently available laser ultrasound inspection systems that use a laser beam in the form of a point. Further, these operations may be performed without contact to the surface of a test object in contrast to laser ultrasound inspection systems that use piezoelectric transducers.

Figure 26:
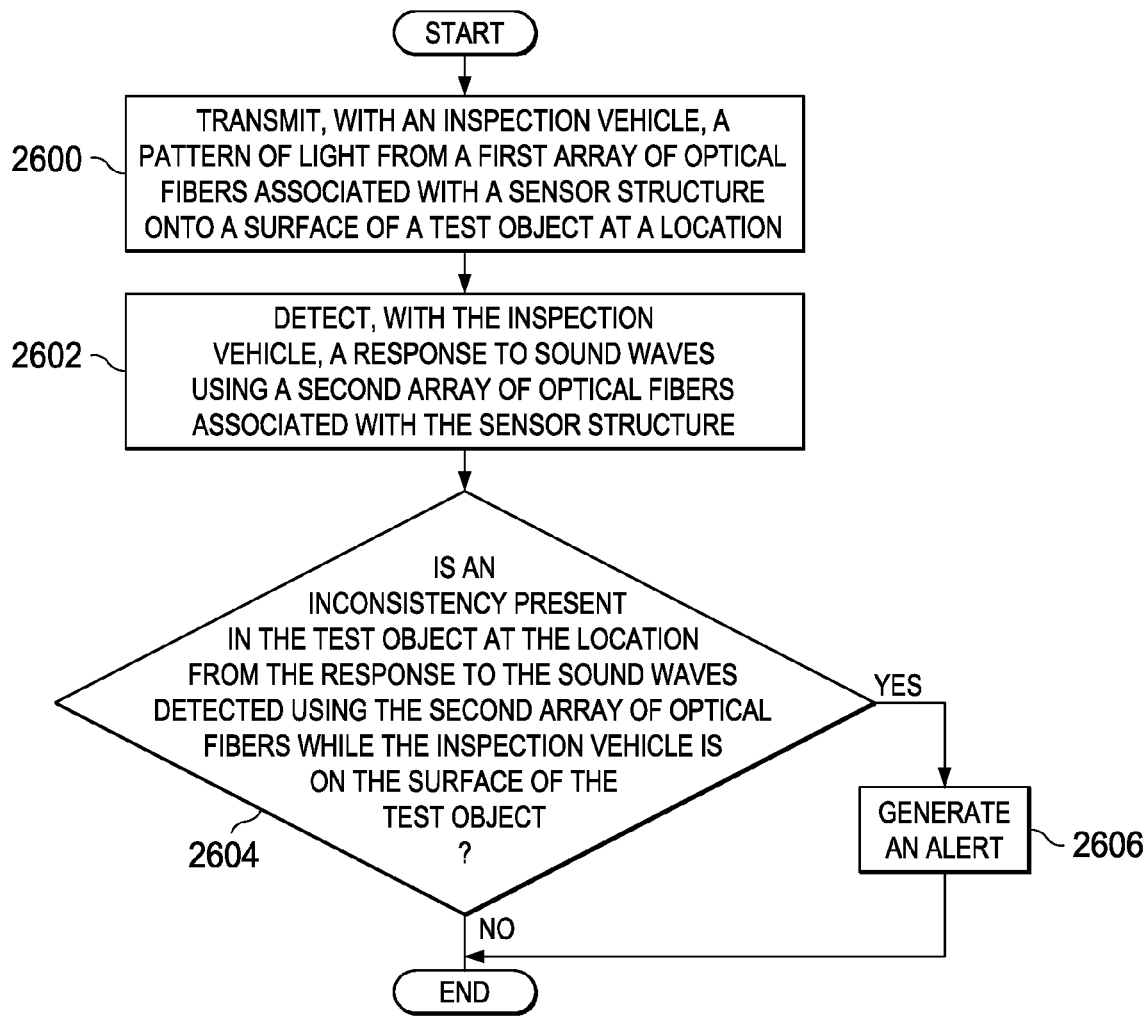
FIG. 26 is an illustration of a flowchart of a process for inspecting a test object in accordance with an illustrative embodiment.

Turning now to FIG. 26, an illustration of a flowchart of a process for inspecting a test object is depicted in accordance with an illustrative embodiment. The process illustrated in FIG. 26 may be implemented in inspection environment 1400 in FIG. 14. In particular, the process may be implemented using inspection vehicle 1408 in FIG. 14.

The process begins with an inspection vehicle transmitting a pattern of light from a first array of optical fibers associated with a sensor structure onto a surface of a test object at a location (operation 2600). The pattern of light is configured to cause sound waves in the test object when the pattern of light encounters the test object. The test object may be an aircraft, such as aircraft 1902 in FIG. 19.

The inspection vehicle then detects a response to sound waves using a second array of optical fibers associated with the sensor structure (operation 2602). A determination is then made as to whether an inconsistency is present in the test object at the location from the response to the sound waves detected using the second array of optical fibers while the inspection vehicle is on the surface of the test object (operation 2604).

This determination may be made using a number of different components. For example, the determination may be made by a controller in the inspection vehicle, a computer in communication with the inspection vehicle, or some other suitable component.

If an inconsistency is not present, the process terminates. Otherwise, if an inconsistency is determined to the present, an alert is generated (operation 2606), with the process terminating thereafter. This alert may be a report, a message, an audio alert, or some other suitable type of alert. The alert also may be stored in a log or other data structure. The alert may include an identification of the location at which the inconsistency is present.

Figure 27:
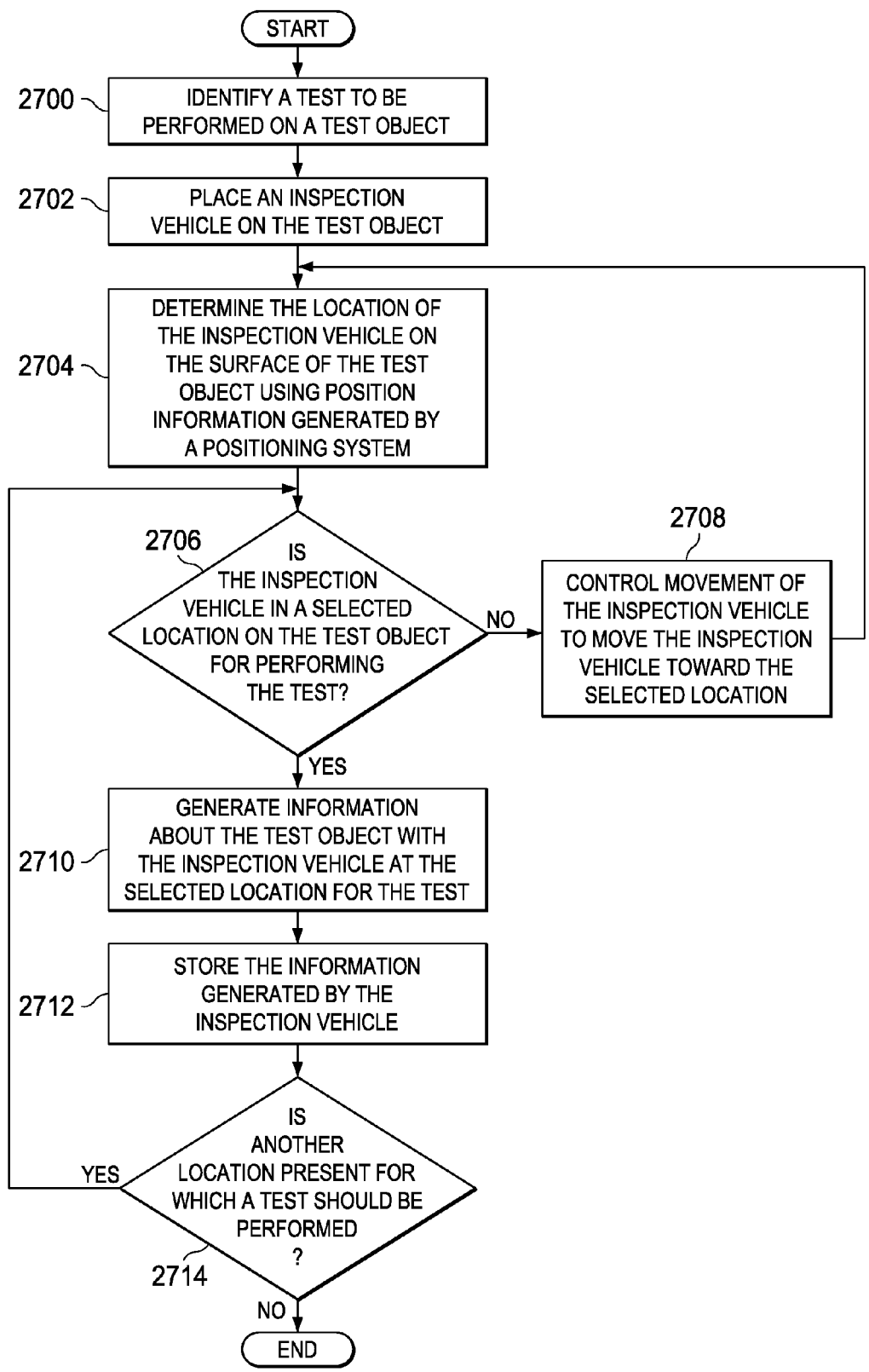
FIG. 27 is an illustration of a flowchart of a process for inspecting a test object in accordance with an illustrative embodiment.

With reference now to FIG. 27, an illustration of a flowchart of a process for inspecting a test object is depicted in accordance with an illustrative embodiment. The process illustrated in FIG. 27 may be implemented in inspection system 1402 to perform inspections of test object 1406 in FIG. 14. The process may be implemented in hardware, software, or a combination of the two. For example, the process may be implemented in controller 1416 in vehicle control module 1504 and test module 1506 in FIG. 15.

The process begins by identifying a test to be performed on a test object (operation 2700). This test may be identified using a database, such as test database 1512 in FIG. 15. In these illustrative examples, the test includes an ultrasound inspection using sensor 1419 in FIG. 14. Of course, other tests may be performed if other types of sensors are present.

Thereafter, an inspection vehicle is placed on the test object (operation 2702). The location of the inspection vehicle on the surface of the test object is determined using position information generated by a positioning system (operation 2704).

A determination is made as to whether the inspection vehicle is in a selected location on the test object for performing the test (operation 2706). If the vehicle is not in the selected location, the process controls the movement of the inspection vehicle to move the inspection vehicle toward the selected location (operation 2708), with the process then returning to operation 2704. Operation 2706 and operation 2708 may be part of a feedback control process for controlling the movement of the inspection vehicle.

Otherwise, if the vehicle is in the selected location in operation 2706, information is generated about the test object with the inspection vehicle at the location for the test (operation 2710). In operation 2710, information is generated about the test object with the inspection vehicle by sending commands to a sensor system associated with the inspection vehicle. As depicted, the sensor system may be sensor system 1410 with sensor 1419 in FIG. 14. The generation of the information in operation 2710 may be implemented using operation 2600 and operation 2602 in FIG. 26. The process then stores the information generated by the inspection vehicle (operation 2712).

A determination is made as to whether another location is present for which a test should be performed (operation 2714). If another location is present, the process proceeds to operation 2706 as described above. Otherwise, the process terminates.

Figure 28:
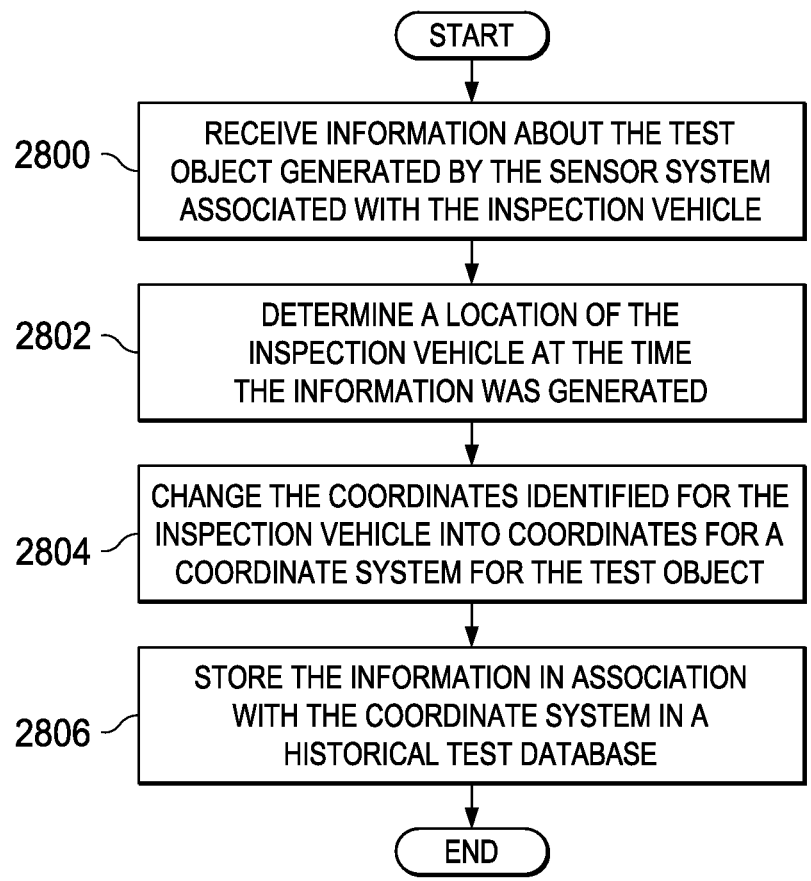
FIG. 28 is an illustration of a flowchart of a process for processing information received from a sensor system on an inspection vehicle in accordance with an illustrative embodiment.

With reference now to FIG. 28, an illustration of a flowchart of a process for processing information received from a sensor system on an inspection vehicle is depicted in accordance with an illustrative embodiment. The process illustrated in FIG. 28 may be implemented in inspection environment 1400 in FIG. 14. In particular, this process may be implemented in test module 1506 in controller 1416 in FIG. 15. This process may be implemented using hardware, software, or a combination of the two. This process is an example of an implementation for operation 2712 in FIG. 27.

The process begins by receiving information about the test object generated by the sensor system associated with the inspection vehicle (operation 2800). The process then determines a location of the inspection vehicle at the time the information was generated (operation 2802). The information received from the sensor system includes timestamps in these illustrative examples. In addition, position information generated by a positioning system also may include timestamps. These timestamps may be correlated to determine the location of the inspection vehicle at the time the information was generated.

The process then changes the coordinates identified for the inspection vehicle into coordinates for a coordinate system for the test object (operation 2804). This coordinate system is one based on the test object being inspected rather than some other test object. This coordinate system may be one defined in a computer-aided design (CAD) model for the test object.

The process then stores the information in association with the coordinate system in a historical test database (operation 2806). This historical test database may be, for example, historical test database 1516. The information is stored with the coordinates and the date and time at which the test was performed. In this manner, other information recorded for the same coordinates on other dates may be analyzed with this information. The process then terminates. This operation may be performed each time information is to be stored in operation 2712 in FIG. 27.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, the operations in FIG. 25 may include an additional number of operations that cause the first pattern of light and the second pattern of light to move across a portion of the test object. These operations may be implemented in operation 2502, operation 2504, or both operations. In other words, the pattern of light transmitted in these operations may include transmitting them such that the pattern is moved over the location by moving one or more mirrors to different positions with a movement device.

This type of scanning may reduce the amount of physical movement of the sensor itself. Also, the speed at which the inspection of the test object is performed may be increased.

Illustrative embodiments of the disclosure may be described in the context of aircraft manufacturing and service method 2900 as shown in FIG. 29 and aircraft 3000 as shown in FIG. 30. Turning first to FIG. 29, an illustration of an aircraft manufacturing and service method is depicted in accordance with an illustrative embodiment. Inspection of test object 1406 in FIG. 14 may be completed during aircraft manufacturing and service method 2900.

During pre-production, aircraft manufacturing and service method 2900 may include specification and design 2902 of aircraft 3000 in FIG. 30 and material procurement 2904.

During production, component and subassembly manufacturing 2906 and system integration 2908 of aircraft 3000 in FIG. 30 takes place. Thereafter, aircraft 3000 in FIG. 30 may go through certification and delivery 2910 in order to be placed in service 2912. While in service 2912 by a customer, aircraft 3000 in FIG. 30 is scheduled for routine maintenance and service 2914, which may include modification, reconfiguration, refurbishment, and other maintenance or service.

Each of the processes of aircraft manufacturing and service method 2900 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 30, an illustration of an aircraft is depicted in which an illustrative embodiment may be implemented. Aircraft 3000 may be one implementation for aircraft 1902 in FIG. 20.

In this example, aircraft 3000 is produced by aircraft manufacturing and service method 2900 in FIG. 29 and may include airframe 3002 with plurality of systems 3004 and interior 3006. Examples of systems 3004 include one or more of propulsion system 3008, electrical system 3010, hydraulic system 3012, and environmental system 3014. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 2900 in FIG. 29.

One or more illustrative embodiments may be used during component and subassembly manufacturing 2906. In the illustrative examples, ultrasound inspection system 204 in FIG. 2 may be used in conjunction with components in inspection system 1402 in FIG. 14 to perform non-destructive inspection of aircraft 3000 and components thereof during different stages of aircraft manufacturing and service method 2900. For example, ultrasound inspection system 204 in FIG. 2 may be used to test different components generated during component and subassembly manufacturing 2906. In particular, ultrasound inspection system 204 may be used to test composite objects that form different parts for aircraft 3000. Further, ultrasound inspection system 204 also may be used to perform inspections during maintenance and service 2914. For example, aircraft 3000 may be inspected during scheduled maintenance for aircraft 3000. Further, ultrasound inspection system 204 also may be used to inspect composite parts used during maintenance and service 2914.

Thus, one or more illustrative embodiments may provide a method and apparatus for inspecting objects. In particular, the illustrative embodiments may be used to inspect objects such as composite parts without the need for physical contact with the part. Further, coupling mediums such as liquids, oils, and other types of coupling media may be unnecessary.

When using an ultrasound inspection system in accordance with an illustrative embodiment, light is used to generate sound waves and detect a response to the sound waves in the test object. With the illustrative embodiments, the movement of the laser beam may only need to be performed in one direction rather than two directions. The illustrative embodiments use a pattern of light rather than a point of light that is scanned across a surface in these illustrative examples.

Further, with the use of optical fibers, the end effector in which the optical fibers are located may be brought closer to the surface of the test object. Further, reduction in power of the laser sources may be achieved. As a result, ultrasound inspection system 204 may be performed without needing an eye-safe room or other safety measures typically associated with higher powered lasers.

In the illustrative examples, non-destructive inspection of a test object may be made using inspection system 1402 in which sensor system 1410 performs ultrasonic inspection of test object 1406. In particular, components from ultrasound inspection system 204 may be implemented within non-destructive evaluation system 1403. Further, sensor 208 and the various components in sensor 208 may be used to implement sensor 1419 in sensor system 1410 in FIG. 14.

In this manner, ultrasound inspection, such as laser ultrasound inspection, may be performed more efficiently through the use of an inspection vehicle. As a result, inspection of a test object may be performed more quickly than with currently available systems.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
   an inspection vehicle configured to move on a surface of a test object;
   a sensor structure associated with the inspection vehicle, wherein the sensor structure comprises:
   a first housing; and
   a second housing;
   a first array of optical fibers associated with the first housing of the sensor structure, wherein the first array of optical fibers is configured to transmit a pattern of light towards the surface of the test object and the pattern of light is configured to cause sound waves in the test object when the pattern of light encounters the test object;
   a second array of optical fibers associated with the second housing of the sensor structure, wherein the second array of optical fibers is configured to detect a response to the sound waves;
   a positioning system configured to determine a location of the inspection vehicle on the test object; and
   a controller configured to control movement of the inspection vehicle using the positioning system and control transmission of the pattern of light by the first array of optical fibers and detection of the response to the sound waves by the second array of optical fibers.

2. The apparatus of claim 1, wherein the controller is configured to determine whether an inconsistency is present based on the response to the sound waves detected by the second array of optical fibers.

3. The apparatus of claim 1 further comprising:
   a support system connected to the inspection vehicle and configured to support the inspection vehicle in response to an undesired release of the inspection vehicle from the surface of the test object.

4. The apparatus of claim 3, wherein the support system comprises:
   an elongate member; and
   a line system connected to the elongate member and to the inspection vehicle, wherein the line system includes the first array of optical fibers and the second array of optical fibers.

5. The apparatus of claim 1, further comprising:
   a camera system associated with the inspection vehicle, wherein the pattern of light is a pattern of first light and wherein the controller is configured to change a position of at least one of the first housing and the second housing such that the pattern of first light transmitted from the first array of optical fibers and a pattern of second light transmitted from the second array of optical fibers to detect the response to the sound waves is aligned on the surface of the test object based on images generated by the camera system.

6. A method for inspecting a test object using an inspection vehicle, the method comprising:
   placing the inspection vehicle on a surface of the test object, the inspection vehicle having a size suitable for moving on the surface of the test object;
   tethering the inspection vehicle to a support system while the inspection vehicle moves on the surface of the test object;
   moving, by the inspection vehicle, on the surface of the test object;
   transmitting a pattern of light from a first array of optical fibers associated with a sensor structure onto a surface of the test object at a location, wherein the pattern of light is configured to cause sound waves in the test object when the pattern of light encounters the test object;
   detecting a response to the sound waves using a second array of optical fibers associated with the sensor structure; and
   determining whether an inconsistency is present in the test object at the location from the response to the sound waves detected using the second array of optical fibers while the inspection vehicle is on the surface of the test object.

7. The method of claim 6 further comprising:
   controlling movement of the inspection vehicle to locations on the surface of the test object using a controller configured to repeat the transmitting, detecting, and determining steps at the locations.

8. The method of claim 6 further comprising:
   supporting the inspection vehicle in response to an undesired release of the inspection vehicle from the surface of the test object using a support system connected to the inspection vehicle.

9. The method of claim 8, wherein the support system comprises an elongate member and a line system connected to the elongate member and to the inspection vehicle, wherein the line system includes the first array of optical fibers and the second array of optical fibers.

10. The method of claim 6, wherein the sensor structure comprises a first housing, in which the first array of optical fibers is associated with the first housing and a second housing in which the second array of optical fibers is associated with the second housing.

11. The method of claim 10, wherein the pattern of light is a pattern of first light and further comprising:
    changing a position of at least one of the first housing and the second housing such that the pattern of first light transmitted from the first array of optical fibers and a pattern of second light transmitted from the second array of optical fibers to detect the response to the sound waves is aligned on the surface of the test object based on images generated by a camera system.

12. An apparatus comprising:
    an inspection vehicle configured to move on a surface of a test object;
    a sensor structure associated with the inspection vehicle;
    a first array of optical fibers associated with the sensor structure, wherein the first array of optical fibers is configured to transmit a pattern of light towards the surface of the test object and the pattern of light is configured to cause sound waves in the test object when the pattern of light encounters the test object;

a second array of optical fibers associated with the sensor structure, wherein the second array of optical fibers is configured to detect a response to the sound waves; and
a support system, including a support arm, configured to tether the inspection vehicle to the support arm while the inspection vehicle moves on the test object.

* * * * *